US008715727B2

(12) United States Patent
Cao et al.

(10) Patent No.: US 8,715,727 B2
(45) Date of Patent: May 6, 2014

(54) TABLET FOR PULSED DELIVERY

(75) Inventors: Bruce Cao, Germantown, MD (US);
Sandra E. Wassink, Frederick, MD
(US); Donald J. Treacy, Jr., Annapolis,
MD (US); Beth A. Burnside, Bethesda,
MD (US); Colin E. Rowlings, Potomac,
IN (US); John A. Bonck, Westminster,
MD (US)

(73) Assignee: Shionogi Inc., Florham Park, NJ (US)

( * ) Notice: Subject to any disclaimer, the term of this patent is extended or adjusted under 35 U.S.C. 154(b) by 1733 days.

(21) Appl. No.: 11/173,929

(22) Filed: Jul. 1, 2005

(65) Prior Publication Data
US 2006/0003005 A1    Jan. 5, 2006

Related U.S. Application Data

(60) Provisional application No. 60/585,202, filed on Jul. 2, 2004.

(51) Int. Cl.
*A61K 9/22* (2006.01)

(52) U.S. Cl.
USPC ........................................................ 424/468

(58) Field of Classification Search
None
See application file for complete search history.

(56) References Cited

U.S. PATENT DOCUMENTS

| | | | |
|---|---|---|---|
| 3,108,046 A | 10/1963 | Harbit | 167/82 |
| 3,870,790 A | 3/1975 | Lowey et al. | 424/19 |
| 4,007,174 A | 2/1977 | Laundon | 260/243 |
| 4,008,246 A | 2/1977 | Ochiai et al. | 260/306.8 |
| 4,018,918 A | 4/1977 | Ayer et al. | 514/24 |
| 4,048,306 A | 9/1977 | Maier et al. | 424/180 |
| 4,131,672 A | 12/1978 | Huffman | 514/204 |
| 4,175,125 A | 11/1979 | Huffman | 514/208 |
| 4,226,849 A | 10/1980 | Schor | 424/19 |
| 4,236,211 A | 11/1980 | Arvesen | 435/32 |
| 4,250,166 A | 2/1981 | Maekawa et al. | 424/81 |
| 4,331,803 A | 5/1982 | Watanabe et al. | 536/7.2 |
| 4,362,731 A | 12/1982 | Hill | 424/256 |
| 4,369,172 A | 1/1983 | Schor et al. | 424/19 |
| 4,399,151 A | 8/1983 | Sjoerdsma et al. | 514/564 |
| 4,430,495 A | 2/1984 | Patt et al. | 536/16.3 |
| 4,435,173 A | 3/1984 | Siposs et al. | 609/155 |
| 4,474,768 A | 10/1984 | Bright | 424/180 |
| 4,517,359 A | 5/1985 | Kobrehel et al. | 536/7.4 |
| 4,525,352 A | 6/1985 | Cole et al. | 424/114 |
| 4,529,720 A | 7/1985 | Cole et al. | 514/191 |
| 4,560,552 A | 12/1985 | Cole et al. | 424/114 |
| 4,568,741 A | 2/1986 | Livingston | 536/16.5 |
| 4,598,045 A | 7/1986 | Masover et al. | 435/34 |
| 4,616,008 A | 10/1986 | Hirai et al. | 514/200 |
| 4,634,697 A | 1/1987 | Hamashima | 514/202 |
| 4,644,031 A | 2/1987 | Lehmann et al. | 524/501 |
| 4,670,549 A | 6/1987 | Morimoto et al. | 536/7.4 |
| 4,672,109 A | 6/1987 | Watanabe et al. | 536/7.2 |
| 4,680,386 A | 7/1987 | Morimoto et al. | 536/7.4 |
| 4,710,565 A | 12/1987 | Livingston et al. | 536/16.5 |
| 4,723,958 A | 2/1988 | Pope et al. | 604/890.1 |
| 4,728,512 A | 3/1988 | Mehta et al. | 424/458 |
| 4,749,568 A | 6/1988 | Reusser et al. | 424/119 |
| 4,755,385 A | 7/1988 | Etienne et al. | 424/154 |
| 4,775,751 A | 10/1988 | McShane | 540/230 |
| 4,794,001 A | 12/1988 | Mehta et al. | 424/458 |
| 4,808,411 A | 2/1989 | Lu et al. | 424/441 |
| 4,812,561 A | 3/1989 | Hamashima et al. | 540/222 |
| 4,828,836 A | 5/1989 | Elger et al. | 424/419 |
| 4,831,025 A | 5/1989 | Godtfredsen et al. | 514/195 |
| 4,835,140 A | 5/1989 | Smith et al. | 514/24 |
| 4,842,866 A | 6/1989 | Horder et al. | 424/468 |
| 4,849,515 A | 7/1989 | Matier et al. | 536/16.5 |
| 4,879,135 A | 11/1989 | Greco et al. | 623/1.48 |
| 4,894,119 A | 1/1990 | Baron, Jr. et al. | 162/168.2 |
| 4,895,934 A | 1/1990 | Matier et al. | 536/16.5 |
| 4,904,476 A | 2/1990 | Mehta et al. | 424/456 |
| 4,915,953 A | 4/1990 | Jordan et al. | 424/473 |
| 4,945,080 A | 7/1990 | Lindstrom et al. | 514/29 |
| 4,945,405 A | 7/1990 | Hirota | 358/516 |
| 4,971,805 A | 11/1990 | Kitanishi et al. | 424/494 |
| 4,990,602 A | 2/1991 | Morimoto et al. | 536/7.4 |
| 5,011,692 A | 4/1991 | Fujioka et al. | 424/426 |
| 5,045,533 A | 9/1991 | Philippe et al. | 514/29 |
| 5,051,262 A | 9/1991 | Panoz et al. | 424/468 |

(Continued)

FOREIGN PATENT DOCUMENTS

| | | | |
|---|---|---|---|
| EP | 0052075 | 11/1981 | A61K 9/32 |
| EP | 0293885 | 12/1988 | C07H 17/08 |

(Continued)

OTHER PUBLICATIONS

Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 Mar. 2002, 1686-1691.

Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).

Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.

Berry et al., Bacteriological Efficacies of Three Macrolides Compared with Those Amoxicillin-Clavulanate Against *Streptococcus pneumoniae* and *Haemophilus influenzae*, Antimicrob Agents Chemother. Dec. 1998, 42(12): 3193-3199.

(Continued)

*Primary Examiner* — Brian Gulledge
*Assistant Examiner* — Snigdha Maewall
(74) *Attorney, Agent, or Firm* — MH2 Technology Law Group

(57) ABSTRACT

A pharmaceutical tablet comprising an immediate release portion containing an active ingredient and a delayed release portion, wherein the delayed release portion comprises an enteric-coated layer and within the enteric-coated layer there is at least one member selected from the group consisting of enteric-coated microparticle dosage forms containing an active ingredient and enteric-coated mini-tablet dosage forms containing an active ingredient, is disclosed.

10 Claims, No Drawings

(56) References Cited

U.S. PATENT DOCUMENTS

| | | | |
|---|---|---|---|
| 5,110,597 A | 5/1992 | Wong et al. | 424/438 |
| 5,110,598 A | 5/1992 | Kwan et al. | 424/438 |
| 5,143,661 A | 9/1992 | Lawter et al. | 264/4.3 |
| 5,158,777 A | 10/1992 | Abramowitz et al. | 424/458 |
| 5,178,874 A | 1/1993 | Kwan et al. | 424/438 |
| 5,182,374 A | 1/1993 | Tobkes et al. | 536/16.5 |
| 5,204,055 A | 4/1993 | Sachs et al. | 419/2 |
| 5,213,808 A | 5/1993 | Bar-Shalom et al. | 424/473 |
| 5,229,131 A | 7/1993 | Amidon et al. | 424/451 |
| 5,230,703 A | 7/1993 | Alon | 604/20 |
| 5,274,085 A | 12/1993 | Amano et al. | 536/7.4 |
| 5,288,503 A | 2/1994 | Wood et al. | 424/497 |
| 5,334,590 A | 8/1994 | DiNinno et al. | 514/210.09 |
| 5,340,656 A | 8/1994 | Sachs et al. | 428/546 |
| 5,358,713 A | 10/1994 | Shimamura | 424/729 |
| 5,387,380 A | 2/1995 | Cima et al. | 264/69 |
| 5,393,765 A | 2/1995 | Infeld et al. | 514/365 |
| 5,395,626 A | 3/1995 | Kotwal et al. | 424/472 |
| 5,395,628 A | 3/1995 | Noda et al. | 424/490 |
| 5,399,723 A | 3/1995 | Iinuma et al. | 549/403 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,422,343 A | 6/1995 | Yamamoto et al. | 514/45 |
| 5,430,021 A | 7/1995 | Rudnic et al. | 514/14 |
| 5,445,829 A | 8/1995 | Paradissis et al. | 424/480 |
| 5,457,187 A | 10/1995 | Gmeiner et al. | 536/25.5 |
| 5,462,747 A | 10/1995 | Radebaugh et al. | 424/465 |
| 5,466,446 A | 11/1995 | Stiefel et al. | 424/78.37 |
| 5,472,708 A | 12/1995 | Chen | 424/451 |
| 5,476,854 A | 12/1995 | Young | 514/254 |
| 5,490,962 A | 2/1996 | Cima et al. | 264/22 |
| 5,508,040 A | 4/1996 | Chen | 424/451 |
| 5,518,680 A | 5/1996 | Cima et al. | 264/401 |
| 5,538,954 A | 7/1996 | Koch et al. | 514/53 |
| 5,543,417 A | 8/1996 | Waldstreicher | 514/284 |
| 5,556,839 A | 9/1996 | Greene et al. | 514/29 |
| 5,567,441 A | 10/1996 | Chen | 424/494 |
| 5,576,022 A | 11/1996 | Yang et al. | 424/472 |
| 5,578,713 A | 11/1996 | McGill, III | 536/18.5 |
| 5,599,557 A | 2/1997 | Johnson et al. | 424/500 |
| 5,607,685 A | 3/1997 | Cimbollek et al. | 424/422 |
| 5,633,006 A | 5/1997 | Catania et al. | 424/441 |
| 5,672,359 A | 9/1997 | Digenis et al. | 424/463 |
| 5,688,516 A | 11/1997 | Raad et al. | 424/409 |
| 5,702,895 A | 12/1997 | Matsunaga et al. | 435/6 |
| 5,705,190 A | 1/1998 | Broad et al. | 424/465 |
| 5,707,646 A | 1/1998 | Yajima et al. | 424/439 |
| 5,719,132 A | 2/1998 | Lin et al. | 514/50 |
| 5,719,272 A | 2/1998 | Yang et al. | 536/7.4 |
| 5,725,553 A | 3/1998 | Moenning | 606/213 |
| 5,733,886 A | 3/1998 | Baroody et al. | 514/24 |
| 5,756,473 A | 5/1998 | Liu et al. | 514/29 |
| 5,780,446 A | 7/1998 | Ramu | 514/34 |
| 5,789,584 A | 8/1998 | Christensen et al. | 540/227 |
| 5,808,017 A | 9/1998 | Chang | 536/7.4 |
| 5,817,321 A | 10/1998 | Alakhov et al. | 424/400 |
| 5,827,531 A | 10/1998 | Morrison et al. | 424/450 |
| 5,837,284 A | 11/1998 | Mehta et al. | 424/459 |
| 5,837,829 A | 11/1998 | Ku | 536/7.4 |
| 5,840,329 A | 11/1998 | Bai | 424/458 |
| 5,840,760 A | 11/1998 | Carraher, Jr. et al. | 514/493 |
| 5,844,105 A | 12/1998 | Liu et al. | 536/18.5 |
| 5,849,776 A | 12/1998 | Czernielewski et al. | 514/398 |
| 5,852,180 A | 12/1998 | Patel | 536/7.4 |
| 5,858,986 A | 1/1999 | Liu et al. | 514/29 |
| 5,864,023 A | 1/1999 | Ku et al. | 536/7.2 |
| 5,869,170 A | 2/1999 | Cima et al. | 428/304.4 |
| 5,872,104 A | 2/1999 | Vermeulen et al. | 514/29 |
| 5,872,229 A | 2/1999 | Liu et al. | 536/18.6 |
| 5,877,243 A | 3/1999 | Sarangapani | 524/139 |
| 5,883,079 A | 3/1999 | Zopf et al. | 514/25 |
| 5,892,008 A | 4/1999 | Ku et al. | 536/18.5 |
| 5,910,322 A | 6/1999 | Rivett et al. | 424/484 |
| 5,919,219 A | 7/1999 | Knowlton | 607/102 |
| 5,919,489 A | 7/1999 | Saleki-Gerhardt et al. | 424/501 |
| 5,919,916 A | 7/1999 | Gracey et al. | 536/7.2 |
| 5,929,219 A | 7/1999 | Hill | 536/7.2 |
| 5,932,710 A | 8/1999 | Liu et al. | 536/18.7 |
| 5,945,124 A | 8/1999 | Sachs et al. | 424/472 |
| 5,945,405 A | 8/1999 | Spanton et al. | 514/29 |
| 5,972,373 A | 10/1999 | Yajima et al. | 424/439 |
| 5,980,942 A | 11/1999 | Katzhendler et al. | 424/465 |
| 5,985,643 A | 11/1999 | Tomasz et al. | 435/243 |
| 5,998,194 A | 12/1999 | Summers, Jr. et al. | 435/252.33 |
| 6,008,195 A | 12/1999 | Selsted | 514/14 |
| 6,010,718 A | 1/2000 | Al-Razzak et al. | 424/464 |
| 6,013,507 A | 1/2000 | Tomasz et al. | 435/252.3 |
| 6,027,748 A | 2/2000 | Conte et al. | 424/458 |
| 6,031,093 A | 2/2000 | Cole et al. | 540/349 |
| 6,048,977 A | 4/2000 | Cole et al. | 540/349 |
| 6,051,255 A | 4/2000 | Conley et al. | 424/482 |
| 6,051,703 A | 4/2000 | Cole et al. | 514/210.06 |
| 6,057,291 A | 5/2000 | Hancock et al. | 514/12 |
| 6,059,816 A | 5/2000 | Moenning | 606/213 |
| 6,063,613 A | 5/2000 | De Lencastre et al. | 435/252.3 |
| 6,063,917 A | 5/2000 | Ascher et al. | 540/217 |
| 6,068,859 A | 5/2000 | Curatolo et al. | 424/490 |
| 6,110,925 A | 8/2000 | Williams et al. | 514/272 |
| 6,117,843 A | 9/2000 | Baroody et al. | 514/24 |
| 6,120,803 A | 9/2000 | Wong et al. | 424/473 |
| 6,127,349 A | 10/2000 | Chasalow | 514/77 |
| 6,132,768 A | 10/2000 | Sachs et al. | 424/458 |
| 6,132,771 A | 10/2000 | Depui et al. | 424/468 |
| 6,136,587 A | 10/2000 | Tomasz et al. | 435/252.3 |
| 6,156,507 A | 12/2000 | Hiramatsu et al. | 435/6 |
| 6,159,491 A | 12/2000 | Durrani | 424/430 |
| 6,162,463 A * | 12/2000 | Lippa | 424/451 |
| 6,162,925 A | 12/2000 | Williams et al. | 548/335.5 |
| 6,183,778 B1 | 2/2001 | Conte et al. | 424/472 |
| 6,187,768 B1 | 2/2001 | Welle et al. | 514/199 |
| 6,214,359 B1 | 4/2001 | Bax | 424/400 |
| 6,218,380 B1 | 4/2001 | Cole et al. | 514/210.06 |
| 6,228,398 B1 | 5/2001 | Devane et al. | 424/484 |
| 6,231,875 B1 | 5/2001 | Sun et al. | 424/401 |
| 6,248,363 B1 | 6/2001 | Patel et al. | 424/497 |
| 6,251,647 B1 | 6/2001 | De Lencastre et al. | 435/193 |
| 6,265,394 B1 | 7/2001 | Sterzycki et al. | 514/203 |
| 6,270,805 B1 | 8/2001 | Chen et al. | 424/497 |
| 6,280,771 B1 | 8/2001 | Monkhouse et al. | 424/484 |
| 6,294,199 B1 | 9/2001 | Conley et al. | 424/468 |
| 6,294,526 B1 | 9/2001 | Higuchi et al. | 514/192 |
| 6,296,873 B1 | 10/2001 | Katzhendler et al. | 424/465 |
| 6,297,215 B1 | 10/2001 | Hancock et al. | 514/12 |
| 6,299,903 B1 | 10/2001 | Rivett et al. | 424/464 |
| 6,306,436 B1 | 10/2001 | Chungi et al. | 424/464 |
| 6,309,663 B1 | 10/2001 | Patel et al. | 424/450 |
| 6,322,819 B1 | 11/2001 | Burnside et al. | 424/494 |
| 6,333,050 B2 | 12/2001 | Wong et al. | 424/473 |
| 6,340,475 B2 | 1/2002 | Shell et al. | 424/469 |
| 6,352,720 B1 | 3/2002 | Martin et al. | 424/464 |
| 6,358,525 B1 | 3/2002 | Guo et al. | 424/464 |
| 6,358,528 B1 | 3/2002 | Grimmett et al. | 424/474 |
| 6,383,471 B1 | 5/2002 | Chen et al. | 424/45 |
| 6,384,081 B2 | 5/2002 | Berman | 514/621 |
| 6,391,614 B1 | 5/2002 | Tomasz et al. | 435/253.2 |
| 6,399,086 B1 | 6/2002 | Katzhendler et al. | 424/405 |
| 6,403,569 B1 | 6/2002 | Achterrath | 514/50 |
| 6,406,717 B2 | 6/2002 | Cherukuri | 424/484 |
| 6,406,880 B1 | 6/2002 | Thornton | 435/32 |
| 6,440,462 B1 | 8/2002 | Raneburger et al. | 424/489 |
| 6,444,796 B1 | 9/2002 | Suh et al. | 536/72 |
| 6,468,964 B1 | 10/2002 | Rowe | 514/6 |
| 6,479,496 B1 | 11/2002 | Wolff | 514/252.17 |
| 6,495,157 B1 | 12/2002 | Pena et al. | 424/433 |
| 6,497,901 B1 | 12/2002 | Royer | 424/468 |
| 6,503,709 B1 | 1/2003 | Bekkaoui et al. | 435/6 |
| 6,506,886 B1 | 1/2003 | Lee et al. | 536/7.2 |
| 6,514,518 B2 | 2/2003 | Monkhouse et al. | 424/427 |
| 6,515,010 B1 | 2/2003 | Franchini et al. | 514/411 |
| 6,515,116 B2 | 2/2003 | Suh et al. | 536/72 |
| 6,530,958 B1 | 3/2003 | Cima et al. | 623/23.51 |
| 6,541,014 B2 | 4/2003 | Rudnic et al. | 424/400 |
| 6,544,555 B2 | 4/2003 | Rudnic et al. | 424/468 |

(56) References Cited

U.S. PATENT DOCUMENTS

| | | | |
|---|---|---|---|
| 6,548,084 B2 | 4/2003 | Leonard et al. | 424/482 |
| 6,550,955 B2 | 4/2003 | D'Silva | 366/130 |
| 6,551,584 B2 | 4/2003 | Bandyopadhyay et al. | 424/78.04 |
| 6,551,616 B1 | 4/2003 | Notario et al. | 424/464 |
| 6,558,699 B2 | 5/2003 | Venkatesh | 424/464 |
| 6,565,873 B1 | 5/2003 | Shefer et al. | 424/426 |
| 6,565,882 B2 | 5/2003 | Rudnic | 424/472 |
| 6,569,463 B2 | 5/2003 | Patel et al. | 424/497 |
| 6,585,997 B2 | 7/2003 | Moro et al. | 424/434 |
| 6,599,884 B2 | 7/2003 | Avrutov et al. | 514/29 |
| 6,605,069 B1 | 8/2003 | Albers et al. | 604/264 |
| 6,605,300 B1 | 8/2003 | Burnside et al. | 424/452 |
| 6,605,609 B2 | 8/2003 | Barbachyn et al. | 514/227.8 |
| 6,605,751 B1 | 8/2003 | Gibbins et al. | 602/41 |
| 6,610,323 B1 | 8/2003 | Lundberg et al. | 424/458 |
| 6,610,328 B2 | 8/2003 | Rudnic et al. | 424/468 |
| 6,617,436 B2 | 9/2003 | Avrutov et al. | 536/72 |
| 6,623,757 B2 | 9/2003 | Rudnic et al. | 424/468 |
| 6,623,758 B2 | 9/2003 | Rudnic et al. | 424/468 |
| 6,624,292 B2 | 9/2003 | Lifshitz et al. | 536/7.2 |
| 6,627,222 B2 | 9/2003 | Rudnic et al. | 424/468 |
| 6,627,743 B1 | 9/2003 | Liu et al. | 536/72 |
| 6,630,498 B2 | 10/2003 | Gudipati et al. | 514/397 |
| 6,632,453 B2 | 10/2003 | Rudnic et al. | 424/468 |
| 6,635,280 B2 | 10/2003 | Shell et al. | 424/469 |
| 6,638,532 B2 | 10/2003 | Rudnic et al. | 424/468 |
| 6,642,276 B2 | 11/2003 | Wadhwa | 514/781 |
| 6,663,890 B2 | 12/2003 | Rudnic et al. | 424/468 |
| 6,663,891 B2 | 12/2003 | Rudnic et al. | 424/468 |
| 6,667,042 B2 | 12/2003 | Rudnic et al. | 424/400 |
| 6,667,057 B2 | 12/2003 | Rudnic et al. | 424/468 |
| 6,669,948 B2 | 12/2003 | Rudnic et al. | 424/400 |
| 6,669,955 B2 | 12/2003 | Chungi et al. | 424/464 |
| 6,673,369 B2 | 1/2004 | Rampal et al. | 424/468 |
| 6,682,759 B2 | 1/2004 | Lim et al. | 424/468 |
| 6,696,426 B2 | 2/2004 | Singh et al. | 514/58 |
| 6,702,803 B2 | 3/2004 | Kupperblatt et al. | 604/890.1 |
| 6,706,273 B1 | 3/2004 | Roessler | 424/422 |
| 6,723,340 B2 | 4/2004 | Gusler et al. | 424/468 |
| 6,723,341 B2 | 4/2004 | Rudnic et al. | 424/468 |
| 6,730,320 B2 | 5/2004 | Rudnic et al. | 424/468 |
| 6,730,325 B2 | 5/2004 | Devane et al. | 424/489 |
| 6,735,470 B2 | 5/2004 | Henley et al. | 604/20 |
| 6,740,664 B2 | 5/2004 | Cagle et al. | 514/311 |
| 6,746,692 B2 | 6/2004 | Conley et al. | 424/468 |
| 6,756,057 B2 | 6/2004 | Storm et al. | 424/472 |
| 6,767,899 B1 | 7/2004 | Kay et al. | 514/62 |
| 6,777,420 B2 | 8/2004 | Zhi et al. | 514/272 |
| 6,783,773 B1 | 8/2004 | Storm et al. | 424/468 |
| 6,818,407 B2 | 11/2004 | Hancock et al. | 435/7.1 |
| 6,824,792 B2 | 11/2004 | Foreman et al. | 424/487 |
| 6,872,407 B2 | 3/2005 | Notario et al. | 424/464 |
| 6,878,387 B1 | 4/2005 | Petereit et al. | 424/490 |
| 6,906,035 B2 | 6/2005 | Hancock et al. | 514/12 |
| 6,929,804 B2 | 8/2005 | Rudnic et al. | 424/468 |
| 6,946,458 B2 | 9/2005 | Turos | 514/210.15 |
| 6,984,401 B2 | 1/2006 | Rudnic et al. | 424/489 |
| 6,991,807 B2 | 1/2006 | Rudnic et al. | 424/468 |
| 7,008,633 B2 | 3/2006 | Yang et al. | 424/422 |
| 2001/0046984 A1 | 11/2001 | Rudnic | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |
| 2002/0015728 A1 | 2/2002 | Payumo et al. | 424/451 |
| 2002/0028920 A1 | 3/2002 | Lifshitz et al. | 536/7.1 |
| 2002/0042394 A1 | 4/2002 | Hogenkamp et al. | 514/53 |
| 2002/0068078 A1 | 6/2002 | Rudnic et al. | 424/408 |
| 2002/0068085 A1 | 6/2002 | Rudnic et al. | 424/464 |
| 2002/0081332 A1 | 6/2002 | Rampal et al. | 424/461 |
| 2002/0103261 A1 | 8/2002 | Ninkov | 514/731 |
| 2002/0106412 A1 | 8/2002 | Rowe et al. | 424/490 |
| 2002/0115624 A1 | 8/2002 | Behar et al. | 514/42 |
| 2002/0119168 A1 | 8/2002 | Rudnic et al. | 424/400 |
| 2002/0136764 A1 | 9/2002 | Rudnic et al. | 424/457 |
| 2002/0136765 A1 | 9/2002 | Rudnic et al. | 424/457 |
| 2002/0136766 A1 | 9/2002 | Rudnic et al. | 424/457 |
| 2002/0150619 A1 | 10/2002 | Rudnic et al. | 424/468 |
| 2002/0197314 A1 | 12/2002 | Rudnic et al. | 424/468 |
| 2003/0012814 A1 | 1/2003 | Rudnic et al. | 424/468 |
| 2003/0018295 A1 | 1/2003 | Henley et al. | 604/20 |
| 2003/0049311 A1 | 3/2003 | McAllister et al. | 424/452 |
| 2003/0064100 A1 | 4/2003 | Rudnic et al. | 424/468 |
| 2003/0073647 A1 | 4/2003 | Chao et al. | 514/42 |
| 2003/0073648 A1 | 4/2003 | Chao et al. | 514/42 |
| 2003/0073826 A1 | 4/2003 | Chao et al. | 536/18.7 |
| 2003/0077323 A1 | 4/2003 | Rudnic et al. | 424/468 |
| 2003/0086969 A1 | 5/2003 | Rudnic et al. | 424/468 |
| 2003/0091627 A1 | 5/2003 | Sharma | 424/465 |
| 2003/0096006 A1 | 5/2003 | Rudnic et al. | 424/468 |
| 2003/0096007 A1 | 5/2003 | Rudnic et al. | 424/468 |
| 2003/0096008 A1 | 5/2003 | Rudnic et al. | 424/468 |
| 2003/0099706 A1 | 5/2003 | Rudnic et al. | 424/468 |
| 2003/0099707 A1 | 5/2003 | Rudnic et al. | 424/468 |
| 2003/0104054 A1 | 6/2003 | Rudnic et al. | 424/468 |
| 2003/0104055 A1 | 6/2003 | Rudnic et al. | 424/468 |
| 2003/0104056 A1 | 6/2003 | Rudnic et al. | 424/468 |
| 2003/0104058 A1 | 6/2003 | Rudnic et al. | 424/468 |
| 2003/0124196 A1 | 7/2003 | Weinbach et al. | 424/499 |
| 2003/0129236 A1 | 7/2003 | Heimlich et al. | 424/470 |
| 2003/0143268 A1 | 7/2003 | Pryce Lewis et al. | 424/464 |
| 2003/0147953 A1 | 8/2003 | Rudnic et al. | 424/468 |
| 2003/0190360 A1 | 10/2003 | Baichwal et al. | 424/470 |
| 2003/0198677 A1 | 10/2003 | Pryce Lewis et al. | 424/471 |
| 2003/0199808 A1 | 10/2003 | Henley et al. | 604/20 |
| 2003/0203023 A1 | 10/2003 | Rudnic et al. | 424/468 |
| 2003/0206951 A1 | 11/2003 | Rudnic et al. | 424/468 |
| 2003/0216555 A1 | 11/2003 | Lifshitz et al. | 536/7.1 |
| 2003/0216556 A1 | 11/2003 | Avrutov et al. | 536/7.2 |
| 2003/0232089 A1 | 12/2003 | Singh et al. | 424/488 |
| 2003/0235615 A1 | 12/2003 | Rudnic | 424/468 |
| 2004/0018234 A1 | 1/2004 | Rudnic et al. | 424/468 |
| 2004/0033262 A1 | 2/2004 | Kshirsagar et al. | 424/468 |
| 2004/0043073 A1 | 3/2004 | Chen et al. | 424/486 |
| 2004/0047906 A1 | 3/2004 | Percel et al. | 424/468 |
| 2004/0048814 A1 | 3/2004 | Vanderbist et al. | 514/29 |
| 2004/0052842 A1 | 3/2004 | Rudnic et al. | 424/468 |
| 2004/0058879 A1 | 3/2004 | Avrutov et al. | 514/29 |
| 2004/0091528 A1 | 5/2004 | Rogers et al. | 424/468 |
| 2004/0126427 A1 | 7/2004 | Venkatesh et al. | 424/469 |
| 2004/0176737 A1 | 9/2004 | Henley et al. | 604/501 |
| 2004/0219223 A1 | 11/2004 | Kunz | 424/489 |
| 2004/0253249 A1 | 12/2004 | Rudnic et al. | 424/184.1 |
| 2004/0265379 A1 | 12/2004 | Conley et al. | 424/465 |
| 2005/0053658 A1 | 3/2005 | Venkatesh et al. | 424/468 |
| 2005/0064033 A1 | 3/2005 | Notario et al. | 424/468 |
| 2005/0064034 A1 | 3/2005 | Li et al. | 424/469 |
| 2005/0163857 A1 | 7/2005 | Rampal et al. | 424/489 |
| 2005/0203076 A1 | 9/2005 | Li et al. | 514/183 |
| 2005/0203085 A1 | 9/2005 | Li et al. | 514/224.5 |
| 2005/0209210 A1 | 9/2005 | Ding et al. | 514/183 |
| 2005/0238714 A1 | 10/2005 | Rudnic et al. | 424/468 |
| 2005/0256096 A1 | 11/2005 | Combrink et al. | 514/183 |
| 2005/0261262 A1 | 11/2005 | Ma et al. | 514/183 |
| 2005/0277633 A1 | 12/2005 | Ma et al. | 514/224.5 |
| 2006/0019985 A1 | 1/2006 | Ma et al. | 514/306 |
| 2006/0019986 A1 | 1/2006 | Ding et al. | 514/306 |
| 2006/0111302 A1 | 5/2006 | Romesberg et al. | 514/18 |

FOREIGN PATENT DOCUMENTS

| | | | |
|---|---|---|---|
| EP | 0436370 | 7/1991 | A61K 9/54 |
| EP | 0652008 | 5/1995 | A61K 31/47 |
| FR | 2585948 | 2/1982 | A61K 9/22 |
| GB | 2087235 | 5/1982 | A61K 9/16 |
| WO | WO 90/08537 | 8/1990 | A61K 31/00 |
| WO | WO 94/27557 | 12/1994 | |
| WO | WO 95/20946 | * 8/1995 | |
| WO | WO 95/30422 | 11/1995 | A61K 31/71 |
| WO | WO 96/04908 | 2/1996 | A61K 31/43 |
| WO | WO 97/22335 | 6/1997 | A61K 9/20 |
| WO | WO 97/43277 | 11/1997 | A61K 31/505 |
| WO | WO 98/22091 | 5/1998 | A61K 9/10 |
| WO | WO 98/46239 | 10/1998 | A61K 31/71 |

(56) References Cited

FOREIGN PATENT DOCUMENTS

| WO | WO 99/03453 | 1/1999 | ............... A61K 9/50 |
|---|---|---|---|
| WO | WO 99/40097 | 8/1999 | ............... C07H 1/00 |
| WO | WO 00/48607 | 8/2000 | ............... A61K 31/70 |
| WO | WO 00/61116 | 10/2000 | ............... A61K 9/20 |
| WO | WO 01/26663 | 4/2001 | ......... A61K 31/7048 |
| WO | WO 02/38577 | 5/2002 | |
| WO | WO 03/029439 | 4/2003 | ............... C12N 1/14 |
| WO | WO 2005/056754 | 6/2005 | |
| WO | WO 2005/070941 | 8/2005 | ........... C07D 498/08 |

OTHER PUBLICATIONS

Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.

Bhargava et al., Pulsed Feeding During Fed-Batch Aspergillus Oryzae Fermentation Leads to Improved Oxygen Mass Transfer, Biotechnol. Prog. 2003, 19, 1091-1094.

Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, pp. 111-117.

Bishai, Comparative Effectiveness of Different Macrolides: Clarithromycin, Azithromycin, and Erythromycin, Johns Hopkins Point of Care Information Technology (POC-IT).

Bradley, *Staphylococcus aureus* pneumonia: Emergence of MRSA in the Community, Semin Respir Crit Care Med. 2005; 26 (6): 643-649.

Brogden et al., Cefixime. A Review of Its Antibacterial Activity. Pharmacokinetic Properties and Therapeutic Potential, Drugs, Oct. 1989 38 (4): 524-50. (Abstract).

Burgess et al., A Time-Kill Evaluation of Clarithromycin and Azithromycin Against Two Extracellular Pathogens and the Development of Resistance, The Annals of Pharmacotherapy: vol. 33, No. 12, pp. 1262-1265. (Abstract).

Byfield et al., Relevance of the Pharmacology of Oral Tegafur to its Use as a 5-FU Pro-Drug., Cancer Treat Rep. Jun. 1985; 69 (6): 645-52. (Abstract).

Cappeltetty et al., Bactericidal Activities of Cefprozil, Penicillin, Cefaclor, Ceflxime, and Loracarbef against Penicillin-Susceptible and —Resistant *Streptococcus pneumoniae* in an In Vitro Pharmacodynamic Infection Model, Antimicrobial Agents and Chemotherapy, May 1996, p. 1148-1152.

Cha et al., Pulsatile Delivery of Amoxicillin Against *Streptococcus pneumoniae*, Journal of Antimicrobial Chemotherapy, Advance Access Published Oct. 14, 2004.

Craig, Antibiotic Selection Factors and Description of a Hospital-Based Outpatient Antibiotic Therapy Program in the USA, Eur J Clin Microbiol Infect Dis. Jul. 1995;14(7):636-42. (Abstract).

Cremieux at al., Ceftriaxone Diffusion into Cardiac Fibrin Vegetation. Qualitative and Quantitative Evaluation by Autoradiography, Fundam Clin Pharmacol. 1991;5(1):53-60. (Abstract).

Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, p. 672-676.

Erah et al., The Stability of Amoxycillin, Clarithromycin and Metronidazole in Gastric Juice: Relevance to the Treatment of Helicobacter Pylori Infection, J Antimicrob Chemother Jan. 1997;39 (1):5-12. (Abstract).

Fang, A Study of the Ethical Considerations and Implications, Prozac Weekly and Sarafem in the Wake of Prozaccis Patent Expiration, 5.22J/10.02J, Biotechnology and Engineering.

Feder et al., Once-Daily Therapy for *Streptococcal pharyngitis* Wtih Amoxicillin, American Academy of Pediatrics, vol. 103(1), Jan. 1999, pp. 47-51.

Freeman et al., The Cyclosporin-Erythromycin Interaction: Impaired First Pass Metabolism in the Pig, Br J Pharmacol. Jul. 1991;103(3):1709-12. (Abstract).

Frimodt-Moller, Correlation Between Pharmacokinetic / Pharmacodyamic Parameters and Efficacy for Antibiotics in the Treatment of Urinary Tract Infection, Int. J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.

Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998;42(8):1996-2001.

Gnarpe et al., Penicillin Combinations Against Multi-Resistant Urinary Pathogens as an Alternative to Gentamycin Treatment, Microbios 1976;16(65-66):201-6. (Abstract).

Gordon et al., Rationale for Single and High Dose Treatment Regimens with Azithromycin, Pediatric Infectious Disease Journal. 23(2) Supplement: S102-S107, Feb. 2004. (Abstract).

Goswick et al., Activities of Azithromycin and Amphotericin B Against Naegleria Fowled In Vitro and in a Mouse Model of Primary Amebic Meningoencephalitis, Antimicrob Agents Chemother. Feb. 2003; 47(2): 524-528.

Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital.

Hickey et al., Production of Enterolysin a by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antitumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffman et al., Pharmacodynamic and Pharmacokinetic Rationales for the Development of an Oral Controlled-Release Amoxicillin Dosage Form, Journal of Controlled Release 54 (1998) 29-37.

Hoffman et al., Influence of Macrolide Susceptibility on Efficacies of Clarithromycin and Azithromycin Against *Streptococcus pneumoniae* in a Murine Lung Infection Model, Antimicrobial Agents and Chemotherapy, Feb. 2003, p. 739-746, vol. 47, No. 2.

Hyde at al., Macrolide Resistance Among Invasive *Streptococcus pneumoniae* Isolates, JAMA. Oct. 17, 2001; 286(15):1857-62. (Abstract).

Iba et al., Comparison Between Continuous Intravenous and Oral Administration of 5-FU with LV, Gan to Kagaku Ryoho. Apr. 1999; 26(5):631-5 (Abstract).

Jacobs, Pharmacodynamic Approach to Antimicrobial Treatment for Respiratory Infections, Department of Pathology, Case Western Reserve University.

Kaplan at al., Macrolide Therapy of Group a Streptococcal pharyngitis: 10 Days of Macrolide Therapy (Clarithromycin) is More Effective in Streptococcal eradication Than 5 Days (Azithromycin), Clin Infect Dis. Jun. 15, 2001;32(12)1798-802. Epub May 21, 2001. (Abstract).

Klugman, Bacteriological Evidence of Antibiotic Failure in Pneumococcal Lower Respiratory Tract Infections, Eur Respir J 2002; 20 Suppl. 36, 3s-8s.

Kramer et al., Statistical Optimisation of Diclofenac Sustained Release Pellets Coated with Polymethacrylic Films, Int J Pharr. Apr. 30, 2003;256(1-2):43-52. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, Oct. 2000. (Abstract).

Laine et al., Frequency and Clinical Outcome of Potentially Harmful Drug Metabolic Interactions in Patients Hospitalized on Internal and

(56) References Cited

OTHER PUBLICATIONS

Pulmonary Medicine Wards: Focus on Warfarin and Cisapride, Therapeutic Drug Monitoring. 22(5):503-509, 2000.

Lamb et al., Ceftriaxone: An Update of its Use in the Management of Community-Acquired and Noscocomial Infections, Drugs. 2002;62(7)1041-89. (Abstract).

Lemer-Tung et al., Pharmacokinetics of Intrapericardial Administration of 5-Fluorouracil, Cancer Chemother Pharmacol. 1997;40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000 (Abstract).

Livermore et al., Activity of Ertapenem Against *Neisseria gonoritioeae*, Journal of Anumicrobial Chemotherapy 2004 54(1)280-281.

Lovmar et al., Kinetics of Macrolide Action, The Josamycin and Erythromycin Cases, J. Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Administration, Journal of Antimicrobial Chemotherapy (2002) 50, 699-706.

Marten et al., Monthly Report, Jul. 2004, Pulsatile Dosing of Antifungal Compounds, UMBC; to Dr. Robert J. Guttendorf, Advancis Pharmaceutical Corp.

Marten et al., Monthly Report, Aug. 2004, Pulsatile Dosing of Antifungal Compounds, UMBC; to Dr. Robert J. Guttendorf, Advances Pharmaceutical Corp.

Mazzei et al., How Macrolide Pharmacodynamics Affect Bacterial Killing, Infect Med 16(sE):22-28, 1999. (Abstract).

Nightingale, Pharmacokinetics and Pharmacodynamics of Newer Macrolides, Pediatric Infectious Disease Journal. 16(4):438-443, Apr. 1997. (Abstract).

Olofinlade et al. Anal Carcinoma: A 15-Year Retrospective Analysis, Scand J Gastroenterol 2000:35;1194-1199.

Pacifico et al., Comparative Efficacy and Safety of 3-Day Azithromycin and 10-Day Penicillin V Treatment of Group A Beta-Hemolytic *Streptococcal pharyngitis* in Children, Antimicroial Agents and Chemotherapy, Apr. 1996, 1005-1008, vol. 40, No. 4. (Abstract).

Parmar-Lapasia et al., A Comparison of Two Macrolide Antibiotics in the Treatment of Community-Acquired Infections, P & T (Pharmacy & Therapeutics), Oct. 2003, vol. 28, No. 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15) 2001: 4267-4269.

Polak, Pharmacokinetics of Amphotericin B and Flucytosine, Postgrad Med J. Sep. 1979;55(647):667-70. (Abstract).

Porter et al., Antibiotics and Infectious Diseases in Otolaryngology—HNS, Grand Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.

Range Rao et al., Influence of Molecular Size and Water Solubility of the Solute on its Release from Swelling and Erosion Controlled Polymeric Matrices, Journal of Controlled Release, 12 (1990) 133-141.

Reza et al., Comparative Evaluation of Plastic, Hydrophobic and Hydrophilic Polymers as Matrices for Controlled-Release Drug Delivery, J. Pharm Pharmaceut Sci, 6(2):282-291, 2003.

Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Mll-ligram Single Oral Dose and Rate of Eradication of Infection in Vaginal Candidiasis, Antimicrob Agents Chemother. May 1990; 34(5):909-10 (Abstract).

Rivkees et al., Dexamethasone Treatment of Virilizing Congenital Adrenal Hyperplasia: The Ability to Achieve Normal Growth, Pediatrics 2000; 106; 767-773.

Roblin et al., In Vitro Activity of a New Ketolide Antibiotic, HMR 3647, Against *Chlamydia pneumoniae*, Antimicrob Agents Chemother. Jun. 1998; 42(6): 1515-1516.

Santini et al., The Potential of Amifostine: From Cytoprotectant to Therapeutic Agent, Haematologica Nov. 1999; 84(ii): 1035-1042.

Sanz et al., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.

Schaad et al., Azithromycin Versus Penicillin V for Treatment of Acute Group A Streptococcal pharyngitis, The Pediatric Infectious Disease Journal: vol. 21(4) Apr. 2002 pp. 304-308.

Schweizer et al., "Single Shot" Prevention in Abdominal Surgery. Antibiotics with Long Half-Life (Cefriaxone, Omidazole) vs. Antibiotics with Short Hatf-Life (Cefazolin, Metronidazole, Clindamycin), Helv Chir Acta. Apr. 1994,60(4):483-8. (Abstract).

Shvartzman et al., Treatment of Streptococcal pharyngitis with Amoxycillin Once a Day, BMJ vol. 306, pp. 1170-1172, May 1, 1993.

Stringer et al., Section 3: Diseases of the Ear, Part 4: Inner Ear, Chapter 46: Ototoxicity, Paparella: vol. II, Otology and Neuro-Otology.

Suda et al., The Synthesis and In Vitro And In Vivo Stability of 5-Fluorouracil Prodrugs Which Possess Serum Albumin binding Potency, Biol Pharm Bull. Sep. 1993;16(9):876-8. (Abstract).

Sandip et al., Controlled Release Formulation of Tramadol Hydrochloride Using Hydrophilic and Hydrophobic Matrix System, AAPS PharmSciTech 2003; 4 (3) Article 31.

Todar's Online Textbook of Bacteriology, Antimicrobial Agents Used in Treatment of Infectious Disease, 2002 Kenneth Todar University of Wisconsin-Madison Department of Bacteriology.

Vanderkooi et al., Antimicrobial Resistance and the *Pneumococcus*, Infectious Diseases and Microbiology, vol. 3, Issue 5, May 2004.

Villalobos et al., Pharmacokinetics and Pharmacodynamics of Antibacterial Agents in Pediatrics: A Practical Approach, Jacksonville Medicine, Aug. 1998.

Waters, Colorectal Cancer-Drug Treatment, Hospital Pharmacist, vol. 11, pp. 179-192, May 2004.

Wattenberg, Prevention of Carcinogenesis of the Respiratory Tract by Chemopreventive Agents Delivered by Aerosol, International Society of Cancer Chemoprevention, vol. 1, No. 5, Jan. 2003.

Whitehead et al., Amoxycillin Release From a Floating Dosage Form Based on Alginates, International Journal of Pharmaceutics 210 (2000) 45-49.

Yousef et al., Combined Action of Amoxycillin and Dicloxacillin Against *Staphylococcus aureus* in Vitro, Pharmazie Sep. 1985; 40(9):650-1. (Abstract).

About Macrolides, About That Bug.com.
Acepromazine Maleate, DRUGS.
Allergy Site Navigator, Drug Classification A-D.
Amoxycillin (As Trihydrate), Moxyvit.
Amoxicillin + Clavulanate, PetPlace.com.
Answers.com, Macrolide.
Antimetabolites, GPnotebook.
Augmentin, Product Information, GlaxoSmithKline, Physicians Desk References, pp. 1421-1433.
Augmentin XR (PDR entry for) (GlaxoSmithKline), (Amoxicillin/Clavulanate Potassium), Extended Release Tablets, Jun. 2004.
Beta Lactam Antibiotics, Health 24.com.
Biaxin XL, Once-Daily Biaxin XL Clarithromycin Extended-Release Tablets, Abbott Laboratories Online.
Biaxin XL, Once-daily, Abbott.
Biaxin, Dosage and Administration.
Biaxin Filmtab, Biaxin XL Filmtab, Biaxin Granules, pp. 1-25, Abbott Laboratories.
Body Chemistry, Acid Alkaline Foods, Acid Reflux? Gas, Add Indigestion, Acid/Alkaline Balance.

(56) References Cited

OTHER PUBLICATIONS

Carers of Crohns, Antibiotics.
Citizen Petition, McNeil Consumer & Specialty Pharmaceuticals, Mar. 19, 2004.
Clarithromycin Extended-Release Scientific Posters Presented to the 39th Interscience Conference on Antimicrobial Agents and Chemotherapy (ICAAC), San Francisco, Sep. 26-29, 1999.
Clearance and the Elimination Rate Constant, Ke (Elimination Rate)—Half-Life, Oct. 14, 2002.
Complementary Medicine Saves Money, Medicine, Greenhealthwatch.com.
Cross-Reference Art Collections, 901-907; USPTO.gov.
Declaration of Michael J. Rybak. from the prosecution history of U.S. Appl. No. 09/792,092; Sep. 23, 2002.
Dispensing Errors With Depakote, New Formulation Creates Confusion, Patient Safety, Practitioners Reporting News, USP Issued Mar. 3, 2001.
Drugs.com, Drug Information for Diclofenac (Topical).
Drug, Bio-Affecting and Body Treating Compositions (Class 424), 475, Sustained or differential release, United States Patent and Trademark Office.
Elimination Rate Constant/Half-Life, Ke (Elimination Rate)—Half-Life, Oct. 14, 2002.
Emulsions.
Encyclopedia Britannica Online, Types of Drugs>Antimicrobial Drugs>Antibiotics>Macrolides.
Excenel, Swine Health Management, Prewean Program, Pfizer Salud Animal.
Fabrication of Metronidazole Strips, 996 Die Pharmazie 50(1995) Februar. No. 2.
Five vs. 10 Days of Therapy for Streptococcal pharyngitis, American Family Physician, Feb. 15, 2001.
Food and Drug Administration Center for Drug Evaluation and Research Approved Drug Products With Therapetutic Equivalence Evaluations, 24th Edition.
Getting a Drug Into the Body: Absorption.
Highlights on Antineoplastic Drugs, Pharmacia, vol. 11. No. 4, 1993.
Jock Itch and Other dermatophytes . . . , Mycolog.
Klarithran, Ranbaxy(SA)(PTY) LTD, Jun. 2005.
Klucel Hydroxypropylcellulose (HPC). Hercules Incorporated.
MedicineNet.com, Generic Name: Acyclovir, Brand Name: Zovirax, Dec. 31, 1997.
Meeting the Challenge of a New Generation of Respiratory Pathogens, MAC.
The Merck Index, An Encyclopedia of Chemicals, Drugs, and Biologicals, Twelfth Edition, pp. 397-398.
Methods of Formulating Controlled Release Products Outside of the Claims of Forest Laboratory Patents U.S. 4,369,172 and U.S. 4,389,393, Technical Information, Dow Chemical, Feb. 1991.
Miconazole, The Merck Index Results—Form View, Monograph No. 06202.
Mode of Action of Macrolides in Blocking Translation During Bacterial Protein Synthesis: Blocking Peptidyltransferase. Doc Kaiser's Microbiology Home Page, Oct. 13, 2004.
Module 8—Therapeutics. May 25, 2002, Newcastle., BPAIIG Immunology/Infectious Diseases Training Programme, Module: Therapeutics.
Monistat, Which Treatment is Right for You?, Vaginal vs. Oral Therapy.
Neisseria Meningitidis, The Doctor's Doctor, Nov. 8, 2004.
New-Generation Aromatase Inhibitor for Breast Cancer. Anastrozole Challenges Tamoxifen in First-Line Therapy, 10th European Cancer Conference (ECCO 10), Vienna, Austria/ Sep. 12-16, 1999.
New Product Newswire, Drug Topics Archive, Aug. 5, 2002.
Nitrofurantoin, Eckerd Prescription Advisor, Feb. 15, 2001.
Nursing, Cancer Nursing: Principles and Practice, Fifth Edition, Jones and Bartlett Publishers, 2000.
Oral Capecitabine Should Improve Convenience of Chemoradiation for Locally Advanced Rectal Cancer-New Treatment Appears to be Safe and Effective, PeerView Press, Chemotherapy (ICAAC), Sep. 27-30, 2002; San Diego, CA., 40th Annual Meeting of Infectious Diseases Society.
Oral Extended (Controlled) Release Dosage Forms, In Vivo Bioequivalence and In Vitro Dissolution Testing, Office of Generic Drugs.
Pharmaceuticals, Pharmacos Unit F2 Pharmaceuticals V 6.0, Eudralex Collection 3AQ19a 1992.
Physicians Desk Reference, PDR 57 Edition 2003, p. 402/Abbott.
Principles of Diagnosis of Infectious Diseases and Antimicrobial Therapy, Chapter 1.
Procardia XL (Nifedipine) Extended Release Tablets for Oral Use, 69-4467-00-8, Pfizer Labs, Aug. 2003.
Summary of Product Characteristics, Doxycycline Capsules. BP 50mg.
Sustained or Differential Release Type, USPTO Classification Definitions (Dec. 2002 Edition) 964.
Sustained-Release Dosage Forms, Degussa, Rohm Pharma Polymers.
Testicular Cancer: Questions and Answers, Cancer Facts, National Cancer Institute, Aug. 14, 2003.
Traditional Chemotherapy, Chapter 25 from Prevention and Therapy of Cancer and Other Common Disease: Alternative and Traditional Approaches; Infomedix 1996.
Bahnmuller, Metabolites of Microorganisms. 248. Synthetic Analogs of Saphenamycin, J. Antibiot (Tokyo). Nov. 1988; 41(11): 1552-60.
Borman, Chemistry Highlights 2005, Chemical & Engineering News, Dec. 19, 2005, vol. 83, No. 51, pp. 15-20.
Cirz et al., Inhibition of Mutation and Combating the Evolution of Antibiotic Resistance, PLOS Biology, Jun. 2005, vol. 3, Issue 6,e176, pp. 1024-1033.
Darst, New Inhibitors Targeting Bacterial RNA Polymerase, TRENDS in Biochemical Sciences, vol. 29, No. 4, Apr. 2004, pp. 159-162.
Dellit, M.D., Tim, University of Washington and Infectious Diseases Society of Washington; Jeffrey Duchin, MD, Public Health-Seattle & King County and University of Washington; Jo Hofmann, MD, Washington State Department of Health and University of Washington; Enka Gurmai Olson, MD, Tacoma-Pierce County Health Department Antibiotic Resistance Task Force, Interim Guidelines for Evaluation and Management of Community-Associated Methicillin-Resistant *Staphylococcus aureus* Skin and Soft Tissue Infections in Outpatient Settings, Sep. 2, 2004.
Geiger et al., Metabolites of Microorganisms. 247. Phenazines from *Streptomyces antibioticus*, Strain Tu 2706, J Antibiot (Tokyo). Nov. 1988;41 (11): 1542-51.
Gorwitz of et al., Strategies for Clinical Management of MRSA in the Community: Summary of an Experts' Meeting Convened by the Centers for Disease Control and Prevention, Department of Health and Human Services Centers for Disease Control and Prevention, Mar. 2006.
Henry, Disabling Resistance Inhibiting Key Protease Prevents Bacteria From Evolving Drug Resistance, Chemical and Engineering News, May 16, 2005, vol. 83, No. 20, p. 8.
Johnson, N.J. Experts Urge Prudent Antibiotic Use, Examiner.Com, The Associated Press, Jul. 31, 2006.
Kitahara et al., Saphenamycin, A Novel Antibiotic From A Strain of *Streptomyces*, J Antibiot (Tokyo). Oct. 1982; 35(10):1412-4.
Laursen at al., Solid-Phase Synthesis of New Saphenamycin Analogues with Antimicrobial Activity, Bioorg. Med. Chem. Let Jan. 21, 2002; 12(2):171-5.
Laursen et al., First Synthesis of Racemic Saphenamycin and Its Enantiomers. Investigation of Biological Activity, Bioorg. Med. Chem. Mar. 6, 2003;11(5):723-31.
Laursen et al., Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003;1(18):3147-53.
Reusser, Inhibition of Ribosomal and RNA Polymerase Functions by Rubradirin and Its Aglycone, J Antibiot (Tokyo). Nov. 1979;32(11):1186-92.
Rihn, et al., Community—Acquired Methicillin-Resistant *Staphylococcus aureus*: An Emerging Problem in the Athletic Population, AM J Sports Med. Dec. 2005;33(12): 1924-9.

(56) References Cited

OTHER PUBLICATIONS

Salmenlinna et al., Community-Acquired Methicillin-Resistant *Staphylococcus aureus*, Finland, Emerg. Infect. Dis. Jun. 2002;8(6):602-7.

Salmenlinna et al., Community-Acquired Methicillin-Resistant *Staphylococcus aureus*, Finland, Emerging Infectious Diseases, vol. 8, No. 6, Jun. 2002, pp. 602-607.

Vandenesch et al., Community-Acquired Methicillin-Resistant *Staphylococcus aureus* Carrying Panton-Valentine Leukocidin Genes: Worldwide Emergence, Emerg. Infect. Dis. Aug. 2003;9(8):978-84.

Can We Prevent Bacteria From Developing Resistance to Antibiotics?, Sep. 2005, AAPS News Magazine 15.

Healthcare-Associated Methicillin Resistant *Staphylococcus aureus* (HA-MRSA), Department of Health and Human Services, Centers for Disease Control and Prevention, Jun. 1, 2005.

Methicillin-Resistant *Staphylococcus aureus*, HealthLink, Medical College of Wisconsin, Information Provided by the Wisconsin Department of Health and Family Services, Article Reviewed: Apr. 10, 2000, 2003 Medical College of Wisconsin.

Methicillin-Resistant *Staphylococcus aureus* (MRSA) Infection, Written by Dr. Alan Johnson, Clinical Scientist, Website: www.mrsasupport.co.uk, Jan. 8, 2005.

The Public's Health, Back-To-School: Review Immunization Records Early, What Doctors and Parents Need to Know About Immunizations and School, vol. 5, No. 7, Jul.-Aug. 2005.

Sulfonamide Class Antibiotics, ChemicalLand21.com.

* cited by examiner

TABLET FOR PULSED DELIVERY

This application claims priority to U.S. Provisional Application Ser. No. 60/585,202 filed Jul. 2, 2004, the disclosures of which are hereby incorporated by reference in their entireties.

This invention relates to a pharmaceutical composition in tablet form that provides for both immediate and enteric release of an active drug agent, and also relates to the use and formulation of such pharmaceutical composition. More particularly, the present invention relates to a drug delivery system, in tablet form, that is comprised of an immediate release portion and a delayed release portion.

In accordance with the invention an immediate release portion of the pharmaceutical composition contains an active ingredient, from which portion the initiation of release of said active agent is not substantially delayed after ingestion of the pharmaceutical composition.

In accordance with the invention a delayed release portion of the pharmaceutical composition contains an active ingredient, from which portion the initiation of release of said active agent is substantially delayed after ingestion of the pharmaceutical composition.

It is an aspect of the invention that the delayed release portion comprises an enteric coated layer, within which enteric coated layer there is a core tablet containing at least one member selected from the group consisting of enteric-coated microparticle dosage forms containing an active ingredient and enteric coated minitablet dosage forms containing an active ingredient.

In accordance with one aspect of the invention there is provided a delayed release portion that comprises a core tablet that includes an enteric coating, such that the core tablet does not disintegrate in the stomach; i.e., the core tablet disintegrates in the intestine. In accordance with a further aspect of the invention there is provided an immediate release portion whereby the enteric coated core tablet has a non-enteric coating over all or a portion of the enteric coating and this non-enteric coating provides for an immediate release of active that is contained therein; i.e., the immediate release portion releases active ingredient in the stomach.

The core tablet includes therein particles and/or mini-tablets ("mini-tabs") that include therein an active agent and that have an enteric coating to thereby delay release of active agent from the particles and/or mini-tablets until a time that is subsequent to the disintegration of the core tablet in the intestine. Additionally, the core tablet may or may not include a dosage of uncoated active ingredient the release of which is initiated at the time that the core tablet disintegrates in the intestine.

In a preferred embodiment of the invention the core tablet, whether comprised of enteric-coated microparticles, enteric-coated mini-tabs, uncoated active ingredient, or combinations of the foregoing, is itself enteric-coated thereby to ensure its disintegration in the post-stomach GI tract.

In an alternative embodiment of the invention the matrix of the core tablet includes enteric materials that maintain the structure of the core tablet to thereby ensure its disintegration in the post-stomach GI tract, whereby coating the core tablet with an enteric coating is not necessary, though is still preferred.

It is to be understood that when it is disclosed herein that a dosage form initiates release after another dosage form, such terminology means that the dosage form is designed to produce, and is intended to produce, such later initiated release. It is known in the art, however, notwithstanding such design and intent, that some "leakage" of active ingredient may occur owing to known imperfections incident to current pharmaceutical manufacturing processes. Such "leakage" whether by flaking, chipping, or other means is not "release" as used herein.

The core tablet may be either, a multiparticulate core: containing one or more pellet types, designed to release drug in the post-stomach portions of the GI tract, wherein the pellet types provide about 1 to 95% of total core tablet weight; or a mini-tab core: containing one or more mini-tabs also designed to release drug in the post-stomach GI tract, wherein the min-tabs provide about 1 to 95% of total core tablet weight. The enteric polymer layer can be produced by spraying a number of different types of enteric polymers on top of the above-described core tablet. Thus, the enteric polymer coating delays the disintegration of the core tablet until the core tablet reaches the intestine. Additionally, the multiparticulates or mini-tabs comprising the core tablet may be formulated with further delayed and/or modified release materials, to thereby further delay and/or modify release of the active drug agents released therefrom.

In one embodiment the immediate release portion may be an immediate release drug layer that can be sprayed on top of the enteric-coated core tablet to thereby serve as an immediate releasing portion of the drug delivery system.

In one embodiment of the invention the immediate release drug layer completely engulfs the enteric polymer coated core tablet.

In one embodiment of the invention the immediate release drug layer does not completely engulf the enteric polymer coating of the core tablet; in this embodiment a portion of the enteric polymer coating is exposed.

In another embodiment of the invention the immediate release portion may comprise one layer of a bi-layer tablet in conjunction with the enteric-coated core tablet, or the immediate release portion may comprise a plurality of layers in a multi-layer tablet in conjunction with the enteric-coated core tablet.

The instant invention is also directed to a process for treating a patient in need of treatment with an active medicinal agent, which comprises administering to the patient the hereinabove and hereinbelow described pharmaceutical compositions containing such an active medicinal agent.

The instant invention is also directed to a method of making the hereinabove and hereinbelow described pharmaceutical compositions.

Although most enteric coatings are generally known in the art to be pH-sensitive coatings, as used herein the term "enteric coating" includes both coatings that are pH-sensitive and coatings that are pH-independent. More particularly the term "enteric coating" as used herein indicates that the coating is one that is selected for its ability to deliver active ingredients to the post-stomach GI tract.

As used herein the term "enteric coated tablet" means a tablet that is capable of delivering one or more pulses of active drug agent into the small intestinal region of the GI tract. Such enteric coated tablet is not limited to tablets engulfed by, or overlayed with, an enteric coating, but includes tablets having matrices comprising enteric materials that maintain the unit integrity of the core tablet at least until such tablet is delivered to the intestine. The core tablet of the instant invention is an enteric coated tablet in that it permits the delivery of a multi-particulate comprised (mini-tab, bead, microparticle, etc.) tablet into the GI tract as an intact unit. It is a beneficial aspect of the invention that the core tablet is passed from the stomach to the intestine substantially intact and that the core tablet does not disintegrate in the stomach.

Generally, in those embodiments wherein the core tablet contains mini-tabs of the desired drug agent, those mini-tabs are formulated so that they are small enough to fit into a standard sized tablet core. The mini-tabs can be coated with an enteric coating that is either a delayed release and/or modified release coating. In a preferred embodiment the mini-tabs are coated with a delayed release coating. In another preferred embodiment there is a plurality of different mini-tabs in that each is coated with a delayed release coating that results in each different mini-tab initiating release of active ingredient therefrom at different times, each of which different times is subsequent to the time at which the core tablet enters the small intestine. Depending on the size of the mini-tabs, a core tablet may comprise one or more mini-tabs each consisting of the same drug agent or different drug agents, along with known pharmaceutical fillers. The core tablet is thereafter coated with an enteric coating that is either a delayed release or a modified release coating. The immediate release portion containing an active drug agent may thereafter be layered over at least a portion of the enteric-coated core tablet to provide an immediate release of a desired active drug agent.

In one embodiment additional enteric materials are used to formulate the matrix of the above-described tablet core to thereby further modify release of active ingredient therefrom. In this embodiment an enteric polymer is sprayed on top of the core tablet, wherein enteric materials are used in formulating the matrix of the tablet core.

In one embodiment additional enteric materials are used to formulate the beads or mini-tabs of the above-described tablet core to thereby further modify release of active ingredient therefrom. In this embodiment an enteric polymer is sprayed on top of the core tablet, wherein enteric materials are used in formulating the beads or mini-tabs of the tablet core.

In one embodiment the core tablet comprises at least one mini-tab and an uncoated dosage of active ingredient, whereby after the core tablet's disintegration in the small intestine the uncoated dosage of active ingredient is immediately released at a first time and thereafter the at least one mini-tab initiates release of the active ingredient contained therein at a second time that is subsequent to said first time. This embodiment delivers at least three separate pulses of active ingredient in that the immediate release portion delivers a first pulse in the stomach, and the uncoated dosage of active ingredient and the at least one mini-tab deliver later-initiated pulses in the intestine, whereby the initiation of release of active ingredient from the at least one mini-tab is subsequent to the initiation of release of active ingredient from the uncoated dosage of active ingredient.

In one preferred embodiment the core tablet comprises at least two different mini-tabs, whereby after the core tablet's disintegration in the small intestine the first of the at least two different mini-tabs initiates release of the active ingredient contained therein at a first time, and the second of the at least two different mini-tabs initiates release of the active ingredient contained therein at a second time that is subsequent to said first time. This embodiment delivers at least three separate pulses of active ingredient in that the immediate release portion delivers a first pulse in the stomach, and the at least two different mini-tabs deliver later-initiated pulses in the intestine, whereby the initiation of release of active ingredient from the second mini-tab is subsequent to the initiation of release of active ingredient from the first mini-tab.

In one embodiment the core tablet comprises at least two mini-tabs and an uncoated dosage of active ingredient, whereby after the core tablet's disintegration in the small intestine the uncoated dosage of active ingredient is immediately released at a first time and thereafter the at least two mini-tabs initiate release of the active ingredients contained therein at second and third times that are each subsequent to said first time. This embodiment delivers at least four separate pulses of active ingredient in that the immediate release portion delivers a first pulse in the stomach, and the uncoated dosage of active ingredient and the at least two mini-tabs deliver later-initiated pulses in the intestine, whereby, the initiation of release of active ingredient from the at least two mini-tabs is subsequent to the initiation of release of active ingredient from the uncoated dosage of active ingredient, and the initiation of release of active ingredient from the second mini-tab is subsequent to the initiation of release of active ingredient from the first mini-tab.

In another preferred embodiment the core tablet comprises at least three different mini-tabs, whereby after the core tablet's disintegration in the small intestine the first of the at least three different mini-tabs initiates release of the active ingredient contained therein at a first time, the second of the at least three different mini-tabs initiates release of the active ingredient contained therein at a second time that is subsequent to said first time, and the third of the at least three different mini-tabs initiates release of the active ingredient contained therein at a third time that is subsequent to said second time. This embodiment delivers at least four separate pulses of active ingredient in that the immediate release portion delivers a first pulse in the stomach, and the at least three different mini-tabs deliver later-initiated pulses in the intestine, whereby the initiation of release of active ingredient from the second mini-tab is subsequent to the initiation of release of active ingredient from the first mini-tab, and the initiation of release of active ingredient from the third mini-tab is subsequent to the initiation of release of active ingredient from the second mini-tab.

In one embodiment the core tablet comprises at least three mini-tabs and an uncoated dosage of active ingredient, whereby after the core tablet's disintegration in the small intestine the uncoated dosage of active ingredient is immediately released at a first time and thereafter the at least three mini-tabs initiate release of the active ingredients contained therein at second, third, and fourth times that are each subsequent to said first time. This embodiment delivers at least five separate pulses of active ingredient in that the immediate release portion delivers a first pulse in the stomach, and the uncoated dosage of active ingredient and the at least three mini-tabs deliver later-initiated pulses in the intestine whereby, the initiation of release of active ingredient from first of the at least three mini-tab is subsequent to the initiation of release of active ingredient from the uncoated dosage of active ingredient, the initiation of release of active ingredient from the second mini-tab is subsequent to the initiation of release of active ingredient from the first mini-tab, and the initiation of release of active ingredient from the third mini-tab is subsequent to the initiation of release of active ingredient from the second mini-tab.

The present invention may be used to decrease the variability of the absorption of any active drug agent, and it is particularly useful for decreasing the absorption variability of antibiotics. The invention is more particularly useful for decreasing the absorption variability of beta-lactam antibiotics, cephalosporin antibioitics, and macrolide antibiotics. Even more particularly, it is useful for decreasing the absorption variabilities of amoxicillin and clarithromycin, both in separate formulations, and in formulations that combine amoxicillin and clarithromycin.

Current multi-particulate and mini-tab tablet delivery systems, as applied to anti-infective agents, cannot prevent the pre-intestinal separation of microparticles or mini-tabs released in the stomach. These components generally exit the stomach through the pyloric valve or by the gastric emptying mechanisms of the stomach. In addition, the current tablet delivery systems are not staged, in other words they typically either dump the entire contents of the core tablet from the stomach into the small intestine as soon as the enteric coating is released, or they comprise a dosage form designed to give steady blood levels, as opposed to pulsatile blood levels, as soon as the enteric coating is released. This dumping of pellets into the stomach, inherent in the current state multi-particulate tablet dosage forms, can lead to pellet spread and a decrease in the strength of the pulses, resulting in significant variations in in vivo pharmacokinetics. Those variations can be expressed in any or all of Cmax, Tmax, Lag Time, and AUC. The dumping can also lead to local site concentration dilution. The present invention avoids these problems through a pulsatile dosing profile, whereby the drug is released in the GI tract in a staged manner, creating an increase and decrease in plasma levels over time. By including multi-particulate and mini-tab components in the core tablet system, these components can be engineered to release drug in a staged, or sequential burst, fashion to achieve pulsatile plasma levels such as are described in U.S. Pat. Nos. 6,544,555 and 6,723,341, the disclosures of which are hereby incorporated in their entireties.

The enteric-coated core tablet of the present invention is large enough that it does not pass through the pyloric sphincter until after the pyloric sphincter opens to discharge stomach contents into the small intestine. The size of the microparticulates or mini-tabs incorporated into the core tablet does not effect the performance of the product since they are enveloped in the core tablet/enteric coating system, that is emptied as a unit into the small intestine. Accordingly, the size of microparticles and mini-tabs that comprise the core tablet can be relatively small in comparison to the core tablet. By grouping all the down stream pulses together in a core tablet and applying an enteric coating over the core tablet so that they remain bundled together while in the stomach the present invention overcomes the earlier-discussed dumping problems. This allows the pellets or mini-tabs to enter the small intestine as a single bulk unit, thereby avoiding the gradual gastric emptying effects that plague the current art. By creating an outer drug layer an immediate release pulse is also provided.

The benefits of the present invention are not limited to a reduction of in vivo pharmacokinetic variabilities. The instant dual phase delivery paradigm is capable of facilitating high dose loading of a desired drug, and may deliver multiple pulses thereof. Additionally, the instant invention can deliver multiple drugs within the same dosing unit. This multi-dosing aspect allows the instant invention to deliver incompatible drug substances from the same tablet core. It also ensures that the delivery of one drug substance, or pulse of a drug substance, is not delivered until the desired previous substance, or pulse of a drug substance is delivered. The tablet of the present invention can also be used to deliver drugs that may be incompatible in the same dosage form, but which, when presented to the small intestine in combination via the core tablet, will work in tandem with respect to improving absorption or combatting specific infectious problems. The instant invention also allows different regions of the GI tract to be specifically targeted for delivery. Also, the invention allows for once-a-day dosing to better ensure patient compliance; this avoids the possibility of overdosing the patient as only a portion of the drug is delivered at any time during the day. Furthermore, the instant invention permits for a smaller tablet size than can be achieved by way of more traditional multi-particulate tablets. In the more traditional multiparticulate tablets the pellets present greater surface area owing to the different functional coatings and different amounts of functional coatings that are applied to the pellets to create the pulsatile release in the GI tract. The traditional microparticulate tablet size is increased further still by the additions of the various fillers that hold the coated pellets together. In the traditional multiparticulate tablet models, much of the volume is occupied by the high polymer content of the individual pellets. In the instant invention, the first pulse is a coated layer on the surface of the enteric-coated core tablet, and the second pulse may be provided by the granulation inside the enteric coated core tablet that may also function as a cushioning agent or binder to hold the third pulse pellets together. Thus, the present invention provides a tablet in which the earlier pulses are concentrated and more dense, thereby presenting less surface area, and hence occupying less volume, in the tablet. Moreover, the instant drug delivery system allows the formulator to engineer pulses that release at any desired time.

The core tablet of the present invention contains an active drug agent in the form of a prepared compactable matrix and/or compacted pellet, bead, or mini-tab. The pharmaceutical active agent is contained within the enteric-coated core tablet for modified delivery, and a drug layer on top of the enteric-coated tablet provides immediate release delivery. By delivering two or more releases of an active drug agent along the GI tract in a pulsatile fashion the instant improvement may be formulated to comport with the Pulsys™ technology. The Pulsys™ technology (which provides for distinct pulsatile releases of active ingredient separated in time) is described at length in U.S. Pat. No. 6,544,555 B2, issued to Rudnic et al.; the disclosures of which are hereby incorporated, by this reference, in their entireties. Like the Pulsys™ technology, the dual phase delivery system of the instant invention provides distinctly discernible pharmacokinetic curves at specific points in time for each of the delivered pulses of active ingredient.

The core tablet may comprise of either or both of a multi-particulate active (pellet or bead) and/or a compressible active granule and/or matrix and/or mini-tab. A matrix could be made up of an active ingredient with enhancers to improve bioavailability or solubiltiy of the active ingredient depending on limitations inherent to the particular active ingredient absorption characteristics. Active ingredient absorption limitations might be influenced by any or all of moisture content, pH, or active transport mechanisms. A typical pellet or multiparticulate active must be "robust" in that it must be capable of withstanding downstream processing activities. These processing operations may include, but are not limited to: wet granulation, extrusion, spheronization, fluid bed drying, fluid bed coating, roller compaction, tablet compression forces, and pan coating.

While the examples and preferred embodiments of the present invention will describe its exceptional utility with regard to antibiotics, the disclosures herein conceive of their application to myriad other active drug agents. Non-limiting examples of such myriad other active drug agents include other anti-infective agents such as the antifungals and the antivirals, and antineoplastic agents.

A wide variety of antibiotics have been used, and will be used, in order to combat bacterial infection. In general, such antibiotics can be administered by a repeated dosing of immediate release dosage forms, which results in poor compliance, or as controlled release formulations (slow release) at higher administered doses. In one embodiment the present invention is directed to providing for an improved antibiotic product.

In accordance with one aspect of the dual phase delivery system of the present invention, there is provided an antibiotic pharmaceutical product, as described hereinabove and hereinbelow, which contains at least two, preferably at least three, antibiotic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antibiotic contained therein at different times after administration of the antibiotic product.

Thus, in accordance with an aspect of the present invention, there is provided a single or unitary antibiotic product that has contained therein at least two, preferably at least three antibiotic dosage forms, each of which has a different release profile, whereby the antibiotic contained in each of such dosage forms is released at different times.

In accordance with a further aspect of the invention, the antibiotic product may be comprised of at least four different dosage forms, each of which starts to release the antibiotic contained therein at different times after administration of the antibiotic product.

The antibiotic product generally does not include more than five dosage forms with different release times.

In accordance with a preferred embodiment, the antibiotic product has an overall release profile such that when administered the maximum serum concentration of the total antibiotic released from the product is reached in less than twelve hours, preferably in less than eleven hours. In an embodiment, the maximum serum concentration of the total antibiotic released from the antibiotic product is achieved no earlier than four hours after administration.

In accordance with one preferred embodiment of the invention, there are at least two dosage forms. One of the at least two dosage forms is an immediate release dosage form whereby initiation of release of the antibiotic therefrom is not substantially delayed after administration of the antibiotic product. The second of the at least two dosage forms is an enteric dosage form, whereby the antibiotic released therefrom is delayed until after initiation of release of the antibiotic from the immediate release dosage form, and is further delayed until after the second dosage form (contained in the core tablet) has passed through the pyloric sphincter of the stomach and into the intestinal portion of the GI tract. More particularly, the antibiotic released from the second of the at least two dosage forms achieves a $C_{max}$ (maximum serum concentration in the serum) at a time after the antibiotic released from the first of the at least two dosage forms achieves a $C_{max}$ in the serum.

In accordance with another preferred embodiment of the invention, there are at least three dosage forms. One of the at least three dosage forms is an immediate release dosage form whereby initiation of release of the antibiotic therefrom is not substantially delayed after administration of the antibiotic product. The second and third of the at least three dosage forms are enteric dosage forms, whereby the antibiotic released therefrom is delayed until after initiation of release of the antibiotic from the immediate release dosage form and is further delayed until after the second and third dosage forms (contained in the core tablet) have passed through the pyloric sphincter of the stomach and into the intestinal portion of the GI tract. More particularly, the antibiotic released from the second of the at least three dosage forms achieves a $C_{max}$ (maximum serum concentration in the serum) at a time after the antibiotic released from the first of the at least three dosage forms achieves a $C_{max}$ in the serum, and the antibiotic released from the third dosage form achieves a $C_{max}$ in the serum after the $C_{max}$ of antibiotic released from the second dosage form.

In accordance with another preferred embodiment of the invention, the antibiotic is a beta-lactam antibiotic, a cephalosporin antibiotic, or a macrolide antibiotic.

In accordance with another preferred embodiment of the invention, the antibiotic is amoxicillin.

In accordance with another preferred embodiment of the invention, the antibiotic is clarithromycin.

In accordance with another preferred embodiment of the invention, the tablet contains both amoxicillin and clarithromycin.

In a more preferred embodiment of the invention, the antibiotic is amoxicillin and the compliment of amoxicillin released from each subsequently releasing dosage form expresses a maximum concentration in the serum that is equal to or exceeds the maximum concentration in the serum that is expressed by the compliment of amoxicillin released by the dosage form immediately preceeding that subsequently-releasing dosage form.

In one embodiment, the second of the at least three dosage forms initiates release of the antibiotic contained therein at least one hour after the first dosage form, with the initiation of the release therefrom generally occurring no more than six hours after initiation of release of antibiotic from the first dosage form of the at least three dosage forms.

In general, when three dosage forms are used, the immediate release dosage form produces a $C_{max}$ for the antibiotic released therefrom within from about 0.5 to about 2 hours, with the second dosage form of the at least three dosage forms producing a $C_{max}$ for the antibiotic released therefrom within about 6 hours. In general, the $C_{max}$ for such second dosage form is achieved no earlier than two hours after administration of the antibiotic product; however, it is possible within the scope of the invention to achieve $C_{max}$ in a shorter period of time.

As hereinabove indicated, the antibiotic product may contain at least three or at least four or more different dosage forms. For example, if the antibiotic product includes a third dosage form, the antibiotic released therefrom reaches a $C_{max}$ at a time later than the $C_{max}$ is achieved for the antibiotic released from each of the first and second dosage forms. In a preferred embodiment, release of antibiotic from the third dosage form is started after initiation of release of antibiotic from both the first dosage form and the second dosage form. In one embodiment, $C_{max}$ for antibiotic release from the third dosage form is achieved within eight hours.

In another embodiment, the antibiotic product contains at least four dosage forms, with each of the at least four dosage forms having different release profiles, whereby the antibiotic released from each of the at least four different dosage forms achieves a $C_{max}$ at a different time.

As hereinabove indicated, in a preferred embodiment, irrespective of whether the antibiotic contains at least two or at least three or at least four different dosage forms each with a different release profile, $C_{max}$ for all the antibiotic released from the antibiotic product is achieved in less than twelve hours, and more generally is achieved in less than eleven hours.

In a preferred embodiment, the antibiotic product is a once a day product, whereby after administration of the antibiotic product, no further product is administered during the day; i.e., the preferred regimen is that the product is administered only once over a twenty-four hour period. Thus, in accordance with the present invention, there is a single administration of an antibiotic product with the antibiotic being released in a manner such that overall antibiotic release is effected with different release profiles in a manner such that the overall $C_{max}$ for the antibiotic product is reached in less than twelve hours. The term single administration means that the total antibiotic administered over a twenty-four hour period is administered at the same time, which can be a single tablet or two or more thereof, provided that they are administered at essentially the same time.

Applicant has found that a single dosage antibiotic product comprised of at least three antibiotic dosage forms each having a different release profile is an improvement over a single dosage antibiotic product comprised of an antibiotic dosage form having a single release profile. Each of the dosage forms of antibiotic in a pharmaceutically acceptable carrier may have one or more antibiotics and each of the dosage forms may have the same antibiotic or different antibiotics.

Notwithstanding that the preferred emodiment is a once-a-day product the dual phase delivery system herein described is not restricted thereto, and may also be used for twice-a-day administration of drugs that have more limited windows of absorption.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antibiotic release from such fourth dosage form may be initiated prior to or after release from the second or third dosage form.

The antibiotic product of the present invention is formulated in a manner such that it is suitable for oral administration.

Alternatively, in formulating an oral delivery capsule system, several tablets may be put into a capsule to produce a unitary antibiotic product.

In formulating an antibiotic product in accordance with the invention, in one embodiment, the immediate release drug layer of the product sprayed onto the enteric coated core tablet generally provides from about 5% to about 85% of the total dosage of antibiotic to be delivered by the product, with such immediate release drug layer generally providing at least 30-40% of the total dosage of the antibiotic to be delivered by the product. In many cases, the immediate release drug layer provides from about 30% to about 40% of the total dosage of antibiotic to be delivered by the product; however, in some cases it may be desirable to have the immediate release drug layer provide for about 5% to about 20% or 75% to about 85% of the total dosage of antibiotic to be delivered by the product.

The remaining dosage forms deliver the remainder of the antibiotic. If more than one delayed release dosage form is used, in one embodiment, each of the delayed release dosage forms may provide about equal amounts of antibiotic; however, they may also be formulated so as to provide different amounts.

In accordance with one embodiment of the present invention, each of the dosage forms may contain the same antibiotic. In accordance with one embodiment of the present invention, each of the dosage forms may contain different antibiotics. In accordance with one embodiment of the present invention each of the dosage forms may contain more than one antibiotic.

In one embodiment, where the composition contains one immediate release component and two delayed release components, the immediate release component provides from 5% to 85% (preferably 30% to 40%), by weight, of the total antibiotic; where there are three delayed release components, the immediate release component provides from 5% to 75%, by weight, of the total antibiotic; and where there are four delayed release components, the immediate release component provides from 5% to 70%, by weight, of the total antibiotic.

With respect to the delayed release components, where there are two delayed release components, the first delayed release component (the one released earlier in time) provides from 5% to 75%, by weight, of the total antibiotic provided by the two delayed release components with the second delayed release component providing the remainder of the antibiotic.

Where there are three delayed release components, the earliest released component provides 5% to 75% by weight of the total antibiotic provided by the three delayed release components, the next in time delayed release component provides from 5% to 75%, by weight, of the antibiotic provided by the three delayed release components and the last in time providing the remainder of the antibiotic provided by the three delayed release components.

When there are four delayed release components, the earliest delayed release component provides from 5% to 75%, by weight, the next in time delayed release component provides from 5% to 75%, by weight, the next in time delayed release component provides from 5% to 75%, by weight, and the last in time delayed release component provides from 5% to 75%, by weight, in each case of the total antibiotic provided by the four delayed release components.

The Immediate Release Component

The materials to be added to the active ingredients for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

The following are non-limiting, representative examples of some antibiotics that may be used in the product of the invention: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, penicillin V, peniciliin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, suflamerazine, sulfamethazine, sulfamethixole, sulfasalazine, sulfisoxazole, sulfapyrizine, sulfadiazine, sulfmethoxazole, sulfapyridine, metronidazole, methenamine, fosfomycin, nitrofurantoin, trimethoprim, clofazimine, co-triamoxazole, pentamidine, and trimetrexate.

The following are non-limiting, representative examples of some antivirals that may be used in the product of the invention: Acyclovir, Amantadine, Amprenavir, Cidofovir, Delavirdine, Didanosine, Famciclovir, Foscamet, Ganciclovir, Indinavir, Interferon, Lamivudine, Nelfinavir, Nevirapine, Palivizumab, Penciclovir, Ribavirin, Rimantadine, Ritonavir, Saquinavir, Stavudine, Trifluridine, Valacyclovir, Vidarabine, Zalcitabine, Zidovudine.

The following are representative examples of some antifungals that may be used in the product of the invention: amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate).

EXAMPLES

General Procedure for Preparing Immediate Release Pellets

Dissolve binder and liquid ingredients in water. Place solid ingredients into a high shear blender (e.g. Glatt) and mix at low impeller speed (300 rpm) for 1 minute. At an impeller speed of 300 rpm and a chopper speed of 2500 rpm, slowly add the prepared binder solution to the dry mix (3-5 minutes). Add additional water as necessary. Continue to mix for 30 sec. Discharge material and transfer to an extruder. Extrude the granulation with a dome extruder at 50-100 rpm through a 0.6-1 mm, or other appropriate, screen. Transfer the extrudate into a spheronizer. Spheronize at 610 rpm for 20-30 sec. Discharge pellets and transfer to a fluidbed dryer (FluidAir). Dry at 60° C. inlet temp and 200 air flow until the loss on drying (LOD) does not change any further (approx. 60 min). Cool down the pellets at 25° C. air temperature for approximately 15 minutes prior to discharge.

General Procedure for Coating Immediate Release Pellets to Make Enteric Release Pulse 3 and Pulse 4

Preparation of the coating solution. Dissolve sodium lauryl sulfate (SLS) and triethyl citrate (TEC) in water using an overhead mixer. Add polymer and mix for 30-45 min. Add Talc and mix for 30-45 min. Sieve dispersion across a 60 mesh screen prior to use. Continue mixing during the entire coating process in the fluidbed. Transfer the pellets to a pre-heated fluidbed dryer (FluidAir). Apply the coating solution to the pellets spraying at 60-65° C. inlet temp, 170-180 scfm air flow and 30 psi atomization air pressure up to 40% weight gain. Dry pellets at 50° C. and 10 psi for 10 minutes, and cool at 30° C. prior to discharge. Sieve the final product across 20-40 mesh. Yield is typically >95%.

General Procedure for Preparing Granulation (Pulse 2)

Dissolve binder in water. Place the active pharmaceutical ingredient into a high shear blender (e.g. Glatt). At impeller speed 300 rpm and chopper speed 2500 rpm, slowly add the binder solution (3-5 minutes). Add additional water if necessary. Continue to mix for 30 sec. Discharge material and transfer to a fluidbed dryer. Dry the granulation at 50° C. for 60 minutes. Mill through a Comil U10 at speed 50 using screen 7A040603122329B(1016)90. Dry in fluidbed for 30 minutes at 50° C. Sieve across a 20 mesh screen.

General Tableting Procedure

Weigh the appropriate amount of pulse 3 and/or 4 pellets, pulse 2 granulation, and remaining tabletting excipients. Combine all components except Magnesium Stearate (lubricant) in a PK blender and mix for 5 minutes. Add the lubricant and mix for an additional 2 minutes. Compress the blend on a tablet press to an appropriate hardness.

General Procedure for Coating Tablets

To prepare enteric coating solution mix L30D and TEC for 30 minutes at low speed using an overhead mixer. In a separate container, mix water and talc, stirring vigorously. Add Talc slurry to the polymer dispersion. Sieve through 60 mesh screen prior to coating process. Keep stirring the dispersion at slow speed throughout the coating process. Coat tablets in a pan coater (LCDS) at 55° C. inlet temperature, 25 cfm air flow, pump setting of 7-10, pan speed 19 rpm, and atomization pressure of 25-26 psi. Up to 8% weight gain is required for this coating procedure. Yields are typically >95%.

General Procedure for Applying Immediate Release Active Coating

Dissolve HPMC in cold water. Add Amoxicillin, stirring with overhead stirrer at medium speed. Use LCDS 20/30 to apply the coating at inlet temp of 55° C., airflow 24 cfm, pump setting 10-12, pan speed 19 rpm, and 25-28 psi atomization air pressure until the desired weight gain is reached.

General Procedure for Optional Immediate Release Cosmetic/Taste Masking Coating

A solution of 7% opadry solution in water is prepared by stirring. The coating is applied at inlet temp of 65° C., airflow 25 cfm, pump setting 8-9, pan speed 19 rpm, and 25 psi atomization air pressure to reach a total weight gain of 3-3.5%.

Example of an Immediate Release Robust Pellet Formulation:

| Ingredient | % |
|---|---|
| Active Pharmaceutical Ingredient | 85-95% |
| Microcrystalline Cellulose | 4-8% |
| Povidone | 1-5% |
| PEG-35 Castor Oil | 0.5-2% |
| Water | As needed |

Example of an Immediate Release Robust Pellet Formulation:

| Ingredient | % |
|---|---|
| Active Pharmaceutical Ingredient | 1-15% |
| Microcrystalline Cellulose | 69-91% |
| Povidone | 3-6% |
| PEG-35 Castor Oil | 5-10% |
| Water | As needed |

These immediate release pellets can also be coated with an enteric or modified release coating to deliver active ingredient to the required locations in the GI tract.

Examples of Core Tablet Formulations:

| Ingredient | % |
|---|---|
| Active Granule | 5-15% |
| Enteric Coated Pellets | 55-75% |
| Microcrystalline Cellulose | 5-10% |
| Povidone K30 | 1-5% |
| Croscarmelose Sodium | 1-5% |
| Magnesium Stearate | 1-3% |
| Active Granule | 20-25% |
| Enteric Coated Pellets | 40-50% |
| Microcrystalline Cellulose | 20-30% |
| Povidone K30 | 1-8% |
| Croscarmellose Sodium | 1-5% |
| Magnesium Stearate | 1-2% |
| Active Granule | 30-40% |
| Enteric Coated Pellets | 1-15% |
| Microcrystalline Cellulose | 40-60% |
| Povidone K30 | 1-5% |
| Croscarmelose Sodium | 1-5% |
| Magnesium Stearate | 1-3% |
| | % W/W |
| Drug Granules | 7.50% |
| Pulsatile Pellet 3 | 15.00% |
| Pulsatile Pellet 4 | 15.00% |
| SMCC | 27.50% |
| Lactose Monohydrate | 27.50% |
| PVP K30 | 3.00% |
| Croscarmellose Na | 3.00% |
| Magnesium Stearate | 1.00% |
| Drug Granules | 7.50% |
| Pulsatile Pellet 3 | 20.00% |
| Pulsatile Pellet 4 | 20.00% |
| SMCC | 21.25% |
| Lactose Monohydrate | 21.25% |
| PVP K30 | 5.00% |
| Croscarmellose Na | 4.00% |
| Magnesium Stearate | 1.00% |
| Drug Granules | 7.50% |
| Pulsatile Pellet 3 | 30.00% |
| Pulsatile Pellet 4 | 30.00% |
| SMCC | 11.75% |
| Lactose Monohydrate | 11.75% |
| PVP K30 | 5.00% |
| Croscarmellose Na | 4.00% |
| Magnesium Stearate | 1.00% |

Enteric Tablet Coating

Any of the enteric or modified release coatings available can be used to layer the core tablet to provide intra-stomach protection thereof and prevent pre-intestinal emptying of the tablet contents. Enteric polymers include, but are not limited to polyethyl acrylate, methyl methacrylate, ethyl acrylate, and trimethylammonioethyl methacrylate chloride copolymers, hydroxypropyl methylcellulose phthalate, hydroxypropyl methylcellulose acetate succinate, cellulose acetate phthalate, ethylvinylacetate phthalate, polyvinylacetate phthalate, and carboxymethlethylcellulose. Tablet contents (i.e. active matrix/pellets) are encapsulated and protected from releasing before the targeted release point. The coating must withstand downstream processing from further tablet compression forces and/or tablet coating operations. In-vivo, the enteric coating should protect the active contents as they pass through the upper GI tract and stomach until reaching the desired trigger point within the small or large intestine. This will ensure that all of the tablet contents will be emptied as a single packet at the target and prevent separation and dilution of the drug during transit.

Examples of Enteric Coating Formulations:

| Ingredient | % |
|---|---|
| Methacrylic Copolymer | 20-60% |
| Talc | 1-30% |
| Triethyl Citrate | 1-20% |
| Sodium Lauryl Sulfate | 0.25-1.0% |
| Water | As needed |
| | % W/W |
| Eudragit L30D-55 | 50.00% |
| Triethyl Citrate | 2.00% |
| Glycerol Mono-Stearate | 2.00% |
| Water | 46.00% |

Drug Layer

The active pharmaceutical layer or drug layer is applied on top of the protected enteric coated core tablet. The active layer delivers the first pulse or immediate release.

| Ingredient | |
|---|---|
| | % |
| Active | 1-40% |
| Hydroxypropylmethylcellulose | 1-10% |
| Water | As needed |
| | % W/W |
| Metronidazole | 20.00% |
| HPMC (low viscosity) | 5.00% |
| Water | 75.00% |

4 Pulse Amoxicllin Enteric Coated Tablet
Amoxicillin Pellet Formulation and Preparation Procedure
Pellet Formulations for Subsequent Coating
The composition of the Amoxicillin trihydrate matrix pellets provided in Table 1.

TABLE 1

Composition of Amoxicillin Matrix Pellets

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

Preparation Procedure for Amoxicillin Matrix Pellets
Blend Amoxicillin and Avicel® PH 101 using a low shear blender.
Add the hydroxypropyl methylcellulose binder solution slowly into the powder blend under continuous mixing.
Extrude the wet mass using an LCI Bench Top Granulator. The diameter of the screen of the Bench Top Granulator is 0.8 mm.
Spheronize the extrudate using a QJ-230 Spheronizer using a small cross section plate.
Dry the spheronized pellets at 60° C. using a fluid bed dryer until the exhaust temperature reaches 40° C.
Pellets between 20 and 40 Mesh were collected for further processing.
Preparation of an Eudragit® L 30 D-55 Aqueous Coating Dispersion
Dispersion Formulation
The composition of the aqueous Eudragit L30D-55 dispersion applied to the amoxicillin matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

Preparation Procedure for an Eudragit® L 30 D-55 Aqueous Dispersion
Suspend triethyl citrate and talc in deionized water.
The TEC/talc suspension is mixed using laboratory mixer.
Add the TEC/talc suspension from slowly to the Eudragit® L 30 D-55 latex dispersion while stirring.
Allow the coating dispersion to stir for one hour prior to application onto the amoxicillin matrix pellets.
Preparation of an Eudragit® S 100 Aqueous Coating Dispersion
Dispersion Formulation
The composition of the aqueous Eudragit® S 100 dispersion applied to the Amoxicillin matrix pellets is provided below in Table 3.

TABLE 3

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

Preparation Procedure for an Eudragit® S 100 Aqueous Dispersion
Part A:
Dispense Eudragit® S 100 powder in deionized water with stirring.
Add ammonium hydroxide solution drop-wise into the dispersion with stirring.
Allow the partially neutralized dispersion to stir for 60 minutes.
Add triethyl citrate drop-wise into the dispersion with stirring and let stir overnight prior to the addition of Part B.
Part B:
Disperse talc in the required amount of water
Stir the dispersion using an overhead laboratory mixer.
Part B is then added slowly to the polymer dispersion in Part A with a mild stirring.
Coating Conditions for the Application of Aqueous Coating Dispersions
The following coating parameters were used for both the Eudragit® L 30 D-55 and Eudragit® S 100 aqueous film coating processes.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2-6 gram per minute |

Coat matrix pellets with L30 D-55 dispersion such that you apply 20% coat weight gain to the pellets.
Coat matrix pellets with S100 dispersion such that you apply 37% coat weight gain to the pellets.

Preparation of Amoxicillin Granulation (Immediate Release Component) for Tabletting

TABLE 4

Composition of Amoxicillin Granulation

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

Blend Amoxicillin and Avicel® PH 101 using a low shear blender.
Add the hydroxypropyl methylcellulose binder solution slowly into the powder blend under continuous mixing.
Dry the granulation at 60° C. using a fluid bed dryer until the exhaust temperature reaches 40° C.
Granules between 20 and 40 Mesh are collected for further processing.

Tabletting of the Amoxicillin Pellets

TABLE 5

Composition of Amoxicillin tablets

| Component | Percentage (%) |
|---|---|
| Amoxicillin granules | 32.5 |
| Avicel PH 200 | 5.0 |
| Amoxicillin L30D-55 coated pellets | 30 |
| Amoxicillin S100 coated pellets | 30 |
| Colloidal silicon dioxide | 1.5 |
| Magnesium stearate | 1.0 |
| Total | 100 |

Blend the Amoxicillin granules, Avicel PH-200, Amoxicillin pellets and colloidal silicon dioxide for 15 minutes in a tumble blender.
Add the magnesium stearate to the blender, and blend for 5 minutes.
Compress the blend on a rotary tablet press.
The fill weight should be adjusted to achieve a 500 mg dose tablet.

General Procedure for Enteric Coating of Tablets

To prepare enteric coating solution mix L30D and TEC for 30 minutes at low speed using an overhead mixer, according to Table 2. In a separate container, mix water and talc, stirring vigorously. Add Talc slurry to the polymer dispersion. Sieve through 60 mesh screen prior to coating process. Keep stirring the dispersion at slow speed throughout the coating process.
Coat tablets in a pan coater (LCDS) at 55° C. inlet temperature, 25 cfm air flow, pump setting of 7-10, pan speed 19 rpm, and atomization pressure of 25-26 psi. Up to 8% weight gain is desired for this coating procedure.

| Coating Equipment | LCDS laboratory Pan Coater |
|---|---|
| pan speed | 19 rpm |
| atomization pressure of | 25-26 psi |
| Inlet Air Temperature | 50-60° C. |
| Outlet Air Temperature | 30 to 33° C. |
| Pump Rate | 7-10 gram per minute |

General Procedure for Applying Immediate Release Active Coating

Dissolve HPMC in cold water. Add Amoxicillin, stirring with overhead stirrer at medium speed. Use LCDS 20/30 to apply the coating at inlet temp of 55° C., airflow 24 cfm, pump setting 10-12, pan speed 19 rpm, and 25-28 psi atomization air pressure until the desired weight gain is reached.

General Procedure for Optional Immediate Release Cosmetic/Taste Masking Coating

A solution of 7% opadry solution in water is prepared by stirring. The coating is applied at inlet temp of 65° C., airflow 25 cfm, pump setting 8-9, pan speed 19 rpm, and 25 psi atomization air pressure to reach a total weight gain of 3-3.5%.

This example makes a complete amoxicillin enteric coated tablet with 4 pulses containing 500-800 mg amoxicillin.

Four Pulse Clarithromycin Enteric Coated Tablet

Clarithromycin Pellet Formulation and Preparation Procedure

Pellet Formulation

The composition of the clarithromycin matrix pellets provided in Table 6.

TABLE 6

Composition of Clarithromycin Pellets

| Component | Percentage (%) |
|---|---|
| Clarithromycin | 50.6 |
| Lactose monohydrate, spray dried | 32.1 |
| Silicified microcrystalline cellulose | 14.6 |
| Polyoxyl 35 Castor Oil* | 1.7 |
| Hydroxypropyl methylcellulose* | 1.0 |
| Total | 100 |

*Hydroxypropyl methylcellulose and Polyoxyl 35 were added as an 8.7% w/w aqueous solution during wet massing.

Preparation Procedure for Clarithromycin Matrix Pellets

Blend clarithromycin, silicified microcrystalline cellulose and lactose monohydrate using a Robot Coupe high shear granulator.
Prepare the binder solution by adding the Polyoxyl to the purified water while stirring. After that is mixed, slowly add the hydroxypropyl methylcellulose and continue to stir until a solution is achieved.
Add binder solution slowly into the powder blend under continuous mixing.
Granulate the powders in the high shear granulator with the binder solution.
Extrude the wet mass using an LCI Bench Top Granulator. The diameter of the screen of the Bench Top Granulator was 1.2 mm.
Spheronize the extrudate using a Model SPH20 Caleva Spheronizer.
Dry the spheronized pellets at 50° C. overnight.
Pellets between 18 and 30 Mesh were collected for further processing Preparation of an Eudragit® L 30 D-55 Aqueous Coating Dispersion Dispersion Formulation The composition of the aqueous Eudragit L30D-55 dispersion applied to the clarithromycin matrix pellets is provided below in Table 7.

TABLE 7

Eudragit® L 30 D-55 Aqueous Coating Dispersion

| Component | Percentage (%) |
|---|---|
| Eudragit® L 30 D-55 | 40.4 |
| Triethyl Citrate | 1.8 |
| Talc | 6.1 |
| Water | 51.7 |
| Solids Content | 20.0 |
| Polymer Content | 12.1 |

Preparation Procedure for an Eudragit® L 30 D-55 Aqueous Dispersion

Suspend triethyl citrate and talc in deionized water.

The TEC/talc suspension is then homogenized using a PowerGen 700 high shear mixer.

Add the suspension from 4.2.2 slowly to the Eudragit® L 30 D-55 latex dispersion while stirring.

Allow the coating dispersion to stir for one hour prior to application onto the clarithromycin matrix pellets.

Preparation of an Eudragit® S 100 Aqueous Coating Dispersion

Dispersion Formulation

The composition of the aqueous Eudragit® S 100 dispersion applied to the clarithromycin matrix pellets is provided below in Table 8.

TABLE 8

Eudragit® S 100 Aqueous Coating Dispersion

| Component | Percentage (%) |
|---|---|
| Part A | |
| Eudragit® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

Preparation Procedure for an Eudragit® S 100 Aqueous Dispersion

Part A:
Dispense Eudragit® S 100 powder in deionized water with stirring.
Add ammonium hydroxide solution drop-wise into the dispersion with stirring.
Allow the partially neutralized dispersion to stir for 60 minutes
Add the triethyl citrate drop-wise to the dispersion and stir for 60 minutes prior to the addition of Part B.

Part B:
Disperse talc in the required amount of water
Homogenize the dispersion using a PowerGen 700D high shear mixer. Part B is then added slowly to the polymer dispersion in Part A with a mild stirring.

Coating Conditions for the Application of Aqueous Coating Dispersions

The following coating parameters were used for coating the matrix pellets with each of the Eudragit® L 30 D-55 and Eudragit® S 100 aqueous film coating.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.6 Bar |
| Pump Rate | 2 gram per minute |

Coat matrix pellets with L30 D-55 dispersion such that you apply 20% coat weight gain to the pellets.

Coat matrix pellets with S100 dispersion such that you apply 37% coat weight gain to the pellets.

Preparation of Clarithromycin Granulation (Immediate Release Component) for Tabletting

TABLE 9

Composition of clarithromycin Granulation

| Component | Percentage (%) |
|---|---|
| clarithromycin powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

Blend clarithromycin and Avicel® PH 101 using a low shear blender.

Add the hydroxypropyl methylcellulose binder solution slowly into the powder blend under continuous mixing.

Dry the granulation at 60° C. using a fluid bed dryer until the exhaust temperature reaches 40° C.

Granules between 20 and 40 Mesh are collected for further processing.

Tabletting of the Clarithromycin Pellets

TABLE 10

Composition of Clarithromycin Tablets

| Component | Percentage (%) |
|---|---|
| clarithromycin granules | 32.5 |
| Avicel PH 200 | 5.0 |
| clarithromycin L30D-55 coated pellets | 30 |
| clarithromycin S100 coated pellets | 30 |
| Colloidal silicon dioxide | 1.5 |
| Magnesium stearate | 1.0 |
| Total | 100 |

Blend the clarithromycin granules, Avicel PH-200, clarithromycin pellets and colloidal silicon dioxide for 15 minutes in a tumble blender.

Add the magnesium stearate to the blender, and blend for 5 minutes.

Compress the blend on a rotary tablet press.

The fill weight should be adjusted to achieve a 500 mg dose tablet.

General Procedure for Enteric Coating of Tablets

To prepare enteric coating solution mix L30D and TEC for 30 minutes at low speed using an overhead mixer, according to Table 2. In a separate container, mix water and talc, stirring vigorously. Add Talc slurry to the polymer dispersion. Sieve through 60 mesh screen prior to coating process. Keep stirring the dispersion at slow speed throughout the coating process.

Coat tablets in a pan coater (LCDS) at 55° C. inlet temperature, 25 cfm air flow, pump setting of 7-10, pan speed 19 rpm, and atomization pressure of 25-26 psi. Up to 8% weight gain is desired for this coating procedure.

| Coating Equipment | LCDS laboratory Pan Coater |
|---|---|
| pan speed | 19 rpm |
| atomization pressure of | 25-26 psi |
| Inlet Air Temperature | 50-60° C. |
| Outlet Air Temperature | 30 to 33° C. |
| Pump Rate | 7-10 gram per minute |

General Procedure for Applying Immediate Release Active Coating

Dissolve HPMC in cold water. Add clarithromycin, stirring with overhead stirrer at medium speed. Use LCDS 20/30 to apply the coating at inlet temp of 55° C., airflow 24 cfm, pump setting 10-12, pan speed 19 rpm, and 25-28 psi atomization air pressure until the desired weight gain is reached.

General Procedure for Optional Immediate Release Cosmetic/Taste Masking Coating

A solution of 7% opadry solution in water is prepared by stirring. The coating is applied at inlet temp of 65° C., airflow 25 cfm, pump setting 8-9, pan speed 19 rpm, and 25 psi atomization air pressure to reach a total weight gain of 3-3.5%.

This makes a complete clarithromycin enteric coated tablet with 4 pulses.

We claim:

1. A once-a-day pharmaceutical tablet, said tablet comprising an immediate release portion containing amoxicillin and a delayed release portion, wherein said delayed release portion comprises an enteric-coated layer and within said enteric-coated layer there is an uncoated dosage of amoxicillin and at least one member selected from the group consisting of enteric-coated microparticle dosage forms containing amoxicillin and enteric-coated minitablet dosage forms containing amoxicillin, and wherein said once-a-day pharmaceutical tablet does not contain clavulanate.

2. The once-a-day pharmaceutical tablet of claim 1, wherein the compliment of amoxicillin released from each subsequently releasing dosage form expresses a maximum concentration in the serum that is equal to or exceeds the maximum concentration in the serum that is expressed by the compliment of amoxicillin released by the dosage form immediately preceeding that subsequently-releasing dosage form.

3. A method for preparing a once-a-day pharmaceutical tablet having an immediate release portion and a delayed release portion for immediate and delayed release delivery of amoxicillin, wherein said once-a-day pharmaceutical tablet does not contain clavulanate, said method comprising the steps of:

(a) formulating a delayed release portion that comprises a core tablet and an enteric coating, such that said core tablet comprises an uncoated dosage of amoxicillin and at least one member selected from the group consisting of enteric-coated microparticle dosage forms containing amoxicillin and enteric-coated mini-tablet dosage forms containing amoxicillin; and such that said enteric coating covers said core tablet; and (b) applying an immediate release portion containing amoxicillin as an immediate release layer over said delayed release portion such that said immediate release layer at least partially covers said delayed release portion.

4. A process for treating a bacterial infection in a host comprising: administering to a host the once-a-day pharmaceutical tablet of claim 1, once daily.

5. A process for treating a bacterial infection in a host comprising: administering to a host the once-a-day pharmaceutical tablet of claim 2, once daily.

6. A process for treating a bacterial infection in a host comprising: administering to a host the once-a-day pharmaceutical tablet produced by the method of claim 3, once daily.

7. The once-a-day pharmaceutical tablet of claim 1, wherein said at least one member selected from the group consisting of enteric-coated microparticle dosage forms containing amoxicillin and enteric-coated minitablet dosage forms containing amoxicillin, is a pH-sensitive dosage form.

8. The once-a-day pharmaceutical tablet of claim 1, wherein said at least one member selected from the group consisting of enteric-coated microparticle dosage forms containing amoxicillin and enteric-coated minitablet dosage forms containing amoxicillin, is a pH-independent dosage form.

9. A process for treating a bacterial infection in a host comprising: administering to a host the once-a-day pharmaceutical tablet of claim 7, once daily.

10. A process for treating a bacterial infection in a host comprising: administering to a host the once-a-day pharmaceutical tablet of claim 8, once daily.

* * * * *